US005643770A

United States Patent [19]

Mason et al.

[11] Patent Number: 5,643,770

[45] Date of Patent: Jul. 1, 1997

[54] RETROVIRAL VECTOR PARTICLES EXPRESSING COMPLEMENT INHIBITOR ACTIVITY

[75] Inventors: James M. Mason, Wallingford; Stephen P. Squinto, Bethany, both of Conn.

[73] Assignee: Alexion Pharmaceuticals, Inc., New Haven, Conn.

[21] Appl. No.: 278,630

[22] Filed: Jul. 21, 1994

[51] Int. Cl.$^6$ .......................... C12N 15/86; C12N 15/48; C07K 14/15; A61K 48/00

[52] U.S. Cl. .................. 435/172.3; 435/69.7; 435/320.1; 424/93.2; 530/350; 536/23.4

[58] Field of Search .............................. 435/320.1, 172.3, 435/69.7; 424/93.2; 530/350; 536/23.4

[56] References Cited

FOREIGN PATENT DOCUMENTS

94/11524 5/1994 WIPO .

OTHER PUBLICATIONS

Takeuchi et al., J. Virol. 68(12):8001–8007 (1994).

"Report and Recommendations of the Panel to Assess the NIH Investment in Research on Gene Therapy," Orkin and Motulsky, Co–chairs, Dec. 7, 1995.

Kennedy et al., Transplantation 57(10):1494–1501 (1994).

Hayashi et al., Transplantation Proceedings 26(3):1243–1244 (1994).

Marschang et al., European Journal of Immunology 25:285–290 (1995).

Mulligan, Science 260:926–932 (1993).

Albrecht and Fleckenstein, "New member of the multigene family of complement control proteins in herpesvirus saimiri" *J. Virol*, 66:3937–3940, 1992.

Albrecht et al., "Herpesvirus saimiri has a gene specifying a homologue of the cellular membrane glycoprotein CD59" *Virology*, 190:527–530, 1992.

Bartholomew et al., "Lysis of oncornaviruses by human serum" *J. Exp Med*, 147:844–853, 1978.

Bartholomew and Esser, "Mechanism of antibody–independent activation of the first component of complement (C1) on retrovirus membranes" *Biochemistry*, 19:2847–2853, 1980.

Cooper et al., "Lysis of RNA tumor viruses by human serum: Direct antibody–independent triggering of the classical complement pathway" *J. Exp Med*, 144:970–984, 1976.

Culver et al., "In vivo gene transfer with retroviral vector–producer cells for treatment of experimental brain tumors" *Science*, 256:1550–1552, 1992.

Isaacs et al., "Vaccinia virus complement–control protein prevents antibody–dependent complement–enhanced neutralization of infectivity and contributes to virulence" *Proc Natl Acad Sci, USA*, 89:628–632, 1992.

McNearney et al., "Herpes simplex virus glycoproteins gC–1 and gC–2 bind to the third component of complement and provide protection against complement–mediated neutralization of viral infectivity" *J Exp Med*, 166:1525–1535, 1987.

Ram et al., "Toxicity studies of retroviral–mediated gene transfer for the treatment of brain tumors" *J Neurosurg*, 79:400–407, 1993.

Rother et al., "Inhibition of complement–mediated cytolysis by the terminal complement inhibitor of herpesvirus saimiri" *J. Virol*, 68:730–737, 1994.

Welsh et al., "Human serum lyses RNA tumur viruses" *Nature*, 257:612–614, 1975.

Welsh et al., "Inactivation and lysis of oncornaviruses by human serum" *Virology*, 74:432–440, 1976.

*Primary Examiner*—Mindy Fleisher
*Assistant Examiner*—Johnny F. Railey, II
*Attorney, Agent, or Firm*—Seth A. Fidel; Maurice M. Klee

[57] ABSTRACT

Modified retroviral vector particles and modified retroviral producer cells producing such particles are provided for facilitating gene therapy procedures involving the transduction of target cells with retroviral vector particles in the presence of complement containing body fluids. The modifications involve genetic alterations to effect the expression by these cells and particles of complement inhibitor activity. The genetic alterations involve the introduction of nucleic acid expression constructs directing the expression of retroviral SU(gp70)/complement inhibitor chimeric proteins into cells from which the producer cells are derived.

17 Claims, 2 Drawing Sheets

RETROVIRAL VECTOR PARTICLES EXPRESSING COMPLEMENT INHIBITOR ACTIVITY

FIELD OF THE INVENTION

The present invention relates to gene therapy mediated by the transduction of primate cells by retroviral vector particles (RVVPs) and, in particular, to the engineering of cells producing RVVPs to provide RVVPs expressing complement inhibitor activity. Such engineered particles are suitable for medical use for the transduction of human and other primate cells without removing the cells from contact with the extracellular fluids of the host organism.

BACKGROUND OF THE INVENTION

I. Retroviruses

The Retroviridae virus family encompasses all viruses containing an RNA genome and producing an RNA-dependent DNA polymerase (reverse transcriptase). The family is divided into three subfamilies: (1) Oncovirinae, including all the oncogenic retroviruses (referred to in the older literature as "oncornaviruses") and several closely related nononcogenic viruses (collectively referred to herein as "oncoretroviruses"); (2) Lentivirinae, the "slow retroviruses," such as the human immunodeficiency virus (HIV) and visna virus; and (3) Spumavirinae, the "foamy" retroviruses that induce persistent infections, generally without causing any clinical disease. The retroviruses may also be classified based upon virion morphology as type B, type C, or type D retroviruses (Weiss et al., (eds), *RNA Tumor Viruses*, Cold Spring Harbor Laboratory, NY, 1985, Vol. 1, pp.31–34, 46–51, and Vol. 2, pp. 2–7). More detailed descriptions of the retroviruses may be found in Weiss et al., 1985, Volumes 1 and 2; Doolittle, et al., *Quart. Rev. Biol.,* 64:1–29, 1979; and Varmus and Brown, *Retroviruses*, p. 53–108, in Berg and Howe, (eds), 1989, *Mobile DNA*, American Society for Microbiology, Washington, DC.

In broadest overview, the life cycle of a retrovirus comprises entry of an infectious retroviral particle into a host cell, integration of the virus' genetic information into the host cell's genome, and production of new infectious retroviral particles by the biosynthetic machinery of the infected host cell. More specifically, upon entering a cell, a retroviral particle initiates a series of interactive biochemical steps that result in the production of a DNA copy of the virus' RNA genome and its integration into the nuclear DNA of the cell. This integrated DNA copy is referred to as a provirus and can be inherited by any daughter cells of the infected cell like any other gene. Genes contained within the integrated provirus may be expressed in the host cell.

All retroviral particles share common morphological, biochemical, and physical properties, including:

(1) A linear, positive-sense, single-stranded RNA genome composed of two identical subunits and making up about 1% of the mass of the virus.

(2) At least three types of proteins encoded by the viral genome, i.e., gag proteins (the group antigen internal structural proteins), pol proteins (the RNA-dependent DNA polymerase and integrase proteins), and env proteins (the viral envelope protein or proteins). These proteins together make up about 60%–70% of the mass of the virus.

(3) Lipid derived from the cell membrane of an infected cell making up about 30%–40% of the mass of the virus.

(4) Carbohydrate associated with the env proteins, making up about 2–4% of the mass of the virus.

(5) An overall spherical morphology with variable surface projections.

(6) An isocahedral capsid structure containing a ribonucleoprotein complex within an internal nucleoid or nucleocapsid shell.

In addition to genes encoding the gag, pol, and env proteins, the genome of the retrovirus includes two long terminal repeat (LTR) sequences, one at each end of the linear genome. These 5' and 3' LTRs serve to promote transcription and polyadenylation of viral mRNAs. Adjacent to the 5' LTR are sequences necessary for reverse transcription of the viral genome (the tRNA primer binding site) and for efficient encapsulation of viral RNA into particles (the Psi site). Other genes may also be found between the 5' and 3' LTRs of the retroviral genome.

If heterologous genes are inserted in between the 5' and 3' LTRs of a retroviral genome, which is then packaged into a functional retroviral particle, the resulting recombinant retroviral particle is capable of carrying the heterologous genes into a host cell. Upon integration of the recombinant retroviral genome into the host cell's genome as part of the proviral DNA, the heterologous genes may be expressed.

These properties and capabilities have led to the development of retroviral vectors, retroviral packaging and producer cells, and retroviral vector particles (collectively referred to as retroviral transduction systems) as efficient means of stably introducing exogenous genes of interest into mammalian cells. Certain retroviruses have been engineered to produce non-infectious retroviral transduction systems that are especially useful in the field of gene therapy. See Anderson, 1992; Miller, 1992; Mulligan, 1983; Mann, 1983; Cone and Mulligan, 1984.

II. Gene Transfer by Oncoretroviral Transduction

Retroviral transduction systems of the type discussed above are able to introduce recombinant nucleic acid molecules into mammalian target cells, and to efficiently integrate DNA molecules containing some or all of the genetic information (sequence) of the introduced recombinant nucleic acid molecule into the genome of the target cell so that the introduced genetic material is replicated and is stably and functionally maintained (and any encoded gene products are expressed) in the cell without the danger of the production of replicating infectious virus. See, for example, Ausubel, et al., 1992.

Oncoretroviral vector particles are particularly useful for genetically modifying mammalian cells, including human cells, because the efficiency with which they can transduce target cells and integrate their genetic information into the target cell genome is higher than that achievable using other systems of introducing exogenous genetic material into cells. Other advantages associated with the use of oncoretroviral vector particles as gene therapy agents include stable expression of transferred genes, capacity to transfer large genes, and lack of cellular cytotoxicity. Additionally, oncoretroviral vector particles may be constructed so as to be capable of transducing mammalian cells from a wide variety of species and tissues.

Successful gene transfer by transduction with a retroviral vector particle (RVVP) requires: 1) incorporation of a gene of interest into a retroviral vector; 2) packaging of vector-derived RNA into a RVVP; 3) binding of the RVVP to the target cell, generally via a cell surface receptor on the target cell; 4) penetration of at least the RNA molecules comprising the viral genome into the target cell (generally associated with penetration of the RVVP and uncoating of the RVVP); 5) reverse transcription of the viral RNA into pre-proviral cDNA; 6) incorporation of the pre-proviral cDNA into preintegration complexes, 7) translocation of the preintegration complexes into the target cell nucleus, 8) generation of stable proviral DNA by integration of the pre-proviral cDNA into the host genome (typically mediated by the viral integrase protein); and 9) expression of the gene of interest. In the in vivo setting (and in some ex vivo settings), the RVVP must survive in the extracellular fluids of the host organism in an active state for a period sufficient to allow binding and penetration of the host target cell by the RVVP.

Oncoretroviral Envelope Proteins: The binding of an RVVP to a receptor on a target cell referred to above is mediated by retroviral envelope proteins. In oncoretroviral virions, as exemplified by the Moloney murine leukemia virus, the envelope proteins responsible for this binding are found as heterodimers of two polypeptides. These polypeptides are both encoded by the env gene and are proteolytically cleaved by cellular proteases from a common precursor, gp80. The p15E envelope protein is a transmembrane polypeptide also referred to in the art as TM. The gp70 envelope glycoprotein (also referred to in the art as the surface or SU protein) associates with p15E through a non-covalent interaction. On a mature retroviral virion, the TM protein is anchored in the viral membrane and the SU protein is attached to the TM protein and is exposed on the surface of the virion. Large numbers of TM/SU heterodimers are found on oncoretroviral virions. In general, an oncoretroviral SU protein includes the following regions: (i) a secretory signal or "leader" sequence; (ii) a receptor binding domain; (iii) a hinge or neck region; and (iv) a body portion. The receptor binding domain of the gp70 protein is essential for the binding of an oncoretroviral virion to a cell surface receptor on a target cell.

Numerous env genes encoding oncoretroviral SU proteins are well known in the art. Such SU-encoding env genes include those from ecotropic murine leukemia viruses, xenotropic murine leukemia viruses, amphotropic murine leukemia viruses, polytropic murine leukemia viruses, and oncoretroviruses infecting a non-murine species such as feline leukemia viruses or a gibbon ape leukemia viruses.

Oncoretroviral env genes and the proteins they encode share a highly conserved structural/functional domains. The nucleotide and, in particular, the amino acid homologies associated with the conserved domains of SU proteins allow those of skill in the art to determine the locations of the various structural/functional domains, even in previously uncharacterized SU proteins, by comparison with the sequences of well characterized SU proteins in which the various structural/functional domains are known. Examples of such well characterized oncoretroviral SU sequences include those of the Moloney murine leukemia virus ecotropic (eco) and xenotropic (xeno) gp70 proteins. Eco gp70 has 469 amino acids. Amino acid residues 1–33 constitute the leader sequence; amino acid residues 34–263 constitute the receptor binding domain; amino acid residues 264–312 constitute the hinge region; and amino acid residues 313–469 constitute the body portion. Xeno gp70 has 443 amino acids. Amino acid residues 1–30 constitute the leader sequence; amino acid residues 31–232 constitute the receptor binding domain; amino acid residues 233–286 constitute the hinge (or neck) region; and amino acid residues 287–443 constitute the body portion.

Gene Therapy: There is active research, including clinical trial research, on treatment of disease by introduction of genetic material into some of the cells of a patient. A variety of diseases may be treated by therapeutic approaches that involve stably introducing a gene into a cell such that the gene may be transcribed and the gene product may be produced in the cell. Diseases amenable to treatment by this approach include inherited diseases, particularly those diseases that are caused by a single gene defect. Many other types of diseases, including acquired diseases, may also be amenable to gene therapy. Examples of such acquired diseases include many forms of cancer, lung disease, liver disease, and blood cell disorders. See Anderson, 1992; Miller, 1992; and Mulligan, 1993.

Delivery of the gene or genetic material into the cell is the first critical step in gene therapy treatment of disease. A variety of methods have been used experimentally to deliver genetic material into cells. Most research has focused on the use of retroviral and adenoviral vectors for gene delivery. As discussed above, RVVPs are particularly attractive because they have the ability to stably integrate transferred gene sequences into the chromosomal DNA of the target cell and are very efficient in stably transducing a high percentage of target cells. Accordingly most clinical protocols for gene therapy use retroviral vectors (see, for example, Miller, 1992; and Anderson, 1992).

Most gene therapy protocols involve treating target cells from the patient ex vivo and then reintroducing the cells into the patient. Patients suffering from several inherited diseases that are each caused by a single gene defect have already received gene therapy treatments. Such treatments generally involve the transduction of the patient's cells in vitro using RVVPs designed to direct the expression of therapeutic molecules, followed by reintroduction of the transduced cells into the patient. In many cases such treatments have provided beneficial therapeutic effects.

For many diseases, however, it will be necessary to introduce the gene into the target cell in situ, because the target cells cannot be removed from and returned to the body. In other cases, cells that are removed from the patient must be maintained in the presence of body fluids until being returned to the body. Stem cells, particularly hematopoietic stem cells, are an especially important type of target cell for gene therapy of inheritable and acquired blood disorders. Such cells are intrinsically unstable in vitro, and tend to differentiate into cells that are less attractive targets for gene therapy, especially when they have been washed free of the fluids that surround them in vivo and transferred into body-fluid-free liquids comprising tissue culture media or the like.

Accordingly, it is desirable to transduce stem cells as quickly as possible, and ex vivo treatment of such cells with RVVPs is best carried out in the cells natural milieu, i.e., in cells that have not been washed or otherwise removed from the body fluids in which they are obtained, e.g., hematopoietic stem cells in bone marrow aspirates. In the case of stem cells in bone marrow, current medical procedures for bone marrow transplant involve mixing an ex vivo bone marrow aspirate (which is inevitably obtained as a mixture of bone marrow and blood) with heparin and tissue culture medium. The condition of such cells, that have been removed from the body but kept in diluted or undiluted fluids of their natural milieu, is referred to hereinafter as the "ex vivo unwashed state".

III. Complement and Retroviral Vector Particles

A longstanding problem associated with the use of RVVPs as gene therapy vectors in cells in vivo or in cells in the ex vivo unwashed state relates to the inactivation of many oncoretroviruses (and RVVPs derived therefrom) by the body fluids (e.g., blood, bone marrow, lymph) of many primates, including Old World monkeys, apes, and humans.

Indeed, it has been known for almost two decades that certain oncoretroviruses are rapidly inactivated in human serum (Welsh et al., 1975), as well as serum from nonhuman primates (Welsh et al., 1976). This problem has precluded the use of such RVVPs for gene therapy in vivo or in the ex vivo unwashed state.

The complement system has long been implicated in the serum mediated inactivation of oncoretroviruses, as serum deficient in C2, C4 or C8 does not cause the detectable release of reverse transcriptase from oncoretroviral virions (Welsh et al., 1975; Cooper, et al., 1976). The protection of active oncoretroviral particles from human complement is thus necessary for the use of the RVVPs to mediate gene therapy in human cells in vivo or in the ex vivo unwashed state. Accordingly, to date, gene transfer by retroviral transduction has been, for the most part, limited to cells that were removed from the extracellular fluids of the host organism (i.e., ex vivo cells that are not in the ex vivo unwashed state) and thus were not subjected to complement attack. This limitation has represented a significant shortcoming of this technology.

The need for methods allowing transduction of primate cells in situ, in vivo, or in the ex vivo unwashed state has resulted in the development of methods designed to prevent the inactivation of retroviruses by human and other primate sera. Such methods have included the removal of cells from the extracellular fluids of the host organism, as discussed above, as well as the masking of virion structures that can activate complement activity by administration of isolated C1s and/or C1q, as discussed below under the subheading "The Direct C1 Binding Mechanism".

Significantly, with regard to the present invention, no previous methods for allowing transduction of primate cells in situ, in vivo, or in the ex vivo unwashed state have included the genetic engineering of cells so as to generate retroviral producer cells producing RVVPs that express complement inhibitor activities.

The Direct C1 Binding Mechanism: Oncoretroviruses that are sensitive to human serum can activate the human classical complement pathway by a mechanism that involves a unique, antibody independent process. This process is found in many primates and is generally not present in other mammals (see Cooper, et al., 1976). This mechanism is activated when complement component C1 binds to retroviral virions directly and triggers the classical complement pathway, just as the pathway is normally activated by an antigen-antibody complex (Bartholomew, et al., 1978). The complement cascade then causes the eventual destruction and elimination of the virus.

Complement component C1 is a large complex protein composed of 3 subunits designated C1q, C1s, and C1r. C1q is itself composed of 18 polypeptide chains of three different types designated A, B, and C. Six molecules each of chains A, B, and C compose the C1q subunit. There are two molecules each of the C1s subunit and the C1r subunit that associate with C1q to form the C1 complement component. The C1q subunit contains multiple identical binding sites for the complement binding regions of immunoglobulin molecules which regions are only exposed upon the formation of an antigen antibody complex. In the classical pathway, the binding of C1q to these regions of antigen-bound antibody molecules causes a conformational change in the C1 complex resulting in the enzymatic activation of C1 to yield an active serine protease. The C1s and C1q subunits both have a molecular weight of approximately 85 kDa, and each is cleaved to smaller molecular weight forms of approximately 57 kDa and 28 kDa during activation of the C1 complex. The 57 kDa forms of C1s and C1q present in the activated C1 complex contain the protease activity.

In the activation of the classical complement pathway by retroviruses via the direct binding of C1, the C1q subunit of C1 binds directly to at least one site on the retroviral virion. In the case of Moloney murine leukemia virus, the p15E viral protein has been identified as the C1 binding receptor. See Bartholomew, et al., 1978. In contrast to the antibody-mediated classical complement pathway, binding by both the C1q subunit and the C1s subunit of the C1 complex is required for complement activation by retroviral particles via this mechanism. Furthermore, the C1s subunit and C1q subunit must bind the viral particle when they are present in a functional C1 complex in order for complement activation to occur by this mechanism. See Bartholomew, et al., 1980.

The C1s subunit is also believed to have a specific binding site for retroviral envelope proteins. It has been shown, using inactive retrovirus, that prebinding with C1s blocks the subsequent activation of the complement cascade by the retrovirus in vitro. See Bartholomew, et al., 1980.

Co-pending U.S. patent application Ser. No. 08/098,944 ("the '944 application"), filed Jul. 28, 1993 in the name of James M. Mason and entitled "Pre-binding of Retroviral Vector Particles with Complement Components to Enable The Performance of Human Gene Therapy In Vivo," discuses the use of free C1q or free C1s to block the subsequent binding and/or activation of the C1 complex by active retrovirus particles including RVVPs.

As described therein, C1s or C1q or a combination thereof are incubated with the RVVPs in vitro to form complexes with the particles. This complex formation blocks the binding sites for C1s and/or C1q and thereby protects the particles from subsequent inactivation or lysis when the RVVPs are exposed to complement. As further described therein, blockade of intact C1 binding to RVVPs can be achieved by the use of fragments of antibodies that bind the viral envelope proteins of RVVPs but lack complement binding regions.

As disclosed in the '944 application, the use of these methods improves the survival of RVVPs in human serum, but does not completely inhibit retroviral inactivation. The reasons for the incomplete nature of the inhibition of retroviral inactivation by these methods have heretofore been unknown, but are now believed to be due in part to the presence of additional RVVP-associated factors, other than the C1 binding factors discussed above, that can bind to antibodies in Old World primate and human blood and thereby activate the complement system. In accordance with copending U.S. patent application Ser. No. 08/278,639, entitled "Retroviral Transduction of Cells in the Presence of Complement", which is being filed concurrently herewith in the names of Russell P. Rother, Scott A. Rollins, William L. Fodor, and Stephen P. Squinto, these factors are present in the form of alpha galactosyl epitopes found as part of retroviral membrane glycoproteins.

The present invention provides new methods and compositions that can be used in conjunction with, or as an alternative to, the blockade of intact C1 binding to RVVPs. The methods of the present invention thus allow the practice of more efficient gene therapy procedures in vivo and in the ex vivo unwashed state.

Although the C1q and C1s polypeptides and antibody fragments used in the practice of the invention of the '944 application act to inhibit the activation of the complement cascade, these polypeptides are not considered to be complement inhibitor molecules, as they do not interact with complement components, but rather act by masking a target viral protein, thereby preventing the activation of complement component C1 by the viral protein. This masking of the target protein occurs without any direct or indirect interaction with any native complement component, and without the alteration of the activity of a native complement component that is associated with the actions of complement inhibitor molecules.

Along these same lines, in copending U.S. patent application Ser. No. 08/278,639, entitled "Retroviral Transduction of Cells in the Presence of Complement", which is being filed concurrently herewith in the names of Russell P. Rother, Scott A. Rollins, William L. Fodor, and Stephen P. Squinto, discusses the use of certain galactosyl sugars to block the binding of certain preformed natural antibodies to RVVPs. Such blockade of antibody binding can block the activation of the complement system by antigen-bound antibodies, and can thus reduce the inactivation of RVVPs by complement. If desired, these methods of using such sugars as well as other methods discussed in the above-referenced application can be used in conjunction with the methods of the present invention to effect even greater reductions of the inactivation of RVVPs by complement. Similarly to the case of the use of C1q and/or C1s discussed above, the blockade of antibody binding upon administration of the galactosyl sugars occurs without any direct or indirect interactions with any native complement components, and without alterations of the activities of any native complement components, which interactions and alterations are associated with the actions of complement inhibitor molecules.

Thus, as used herein, the term "complement inhibitor molecule" refers to any molecule that inhibits complement activity by interacting, either directly or indirectly, with a native complement component or cofactor so as to reduce complement activity, but not to molecules that interfere with complement activation only by masking structures of non-complement components (such as pathogen structures, e.g., retroviral envelope proteins, or antigen-bound antibodies), and not to molecules that interfére with antibody-antigen binding events that can serve to initiate complement activation. As discussed below, numerous molecules are known in the art that act to reduce complement activity, for example, by binding directly to complement components, or by sequestering cofactors such as divalent cations necessary for complement component activity. In accordance with the foregoing discussion, such molecules are referred to herein as complement inhibitor molecules.

IV. The Complement System

The complement system acts in conjunction with other immunological systems of the body to defend against intrusion of cellular and viral pathogens. There are at least 25 complement proteins, which are found as a complex collection of plasma proteins and membrane cofactors. The plasma proteins (which are also found in most other body fluids, such as lymph, bone marrow, and cerebrospinal fluid) make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lyric functions.

The complement cascade progresses via the classical pathway or the alternative pathway. These pathways share many components, and, while they differ in their early steps, both converge and share the same terminal complement components responsible for the destruction of target cells and viruses.

The classical complement pathway is typically initiated by antibody recognition of and binding to an antigenic site on a target cell. This surface bound antibody subsequently reacts with the first component of complement, C1, as discussed above, includes subunits C1s, C1r, and C1q.

The C1q subunit of C1 mediates the binding of C1 both to antigen-antibody complexes and to retroviruses, although, in the case of direct binding to retroviruses, the C1s subunit also has a binding function. The bound C1 undergoes a set of autocatalytic reactions that result in the activation of the C1r subunits, which in turn proteolytically activate the C1s subunits, altering the conformation of C1 so that the active C1s subunits are exposed on the exterior of C1, where they can interact proteolytically with complement components C2 and C4.

C1s cleaves C2 and C4 into C2a, C2b, C4a, and C4b. The function of C2b is poorly understood. C2a and C4b combine to form the C4b,2a complex, which is an active protease known as the C3 convertase. C4b,2a acts to cleave C3 into C3a and C3b. C3a is a relatively weak anaphylatoxin. C4a is a stronger anaphylatoxin, and can induce degranulation of mast cells, resulting in the release of histamine and other mediators of inflammation. C3b has multiple functions. As opsonin, it binds to bacteria, viruses and other cells and particles and tags them for removal from the circulation. C3b can also form a complex with C4b,C2a to produce C4b,2a,3b, or C5 convertase, which cleaves C5 into C5a (another anaphylatoxin), and C5b. C5b combines with C6 yielding C5b,6, and this complex combines with C7 to form the ternary complex C5b,6,7. The C5b,6,7 complex binds C8 at the surface of a cell membrane. Upon binding of C9, the complete membrane attack complex (MAC) is formed (C5b-9) which mediates the lysis of foreign cells, microorganisms, and viruses.

A more complete discussion of the classical complement pathway, as well as a detailed description of the alternative pathway of complement activation, which pathway has also been implicated in the inactivation of RVVPs by human complement, can be found in Roitt, et al., 1988.

V. Inhibitors of the Complement System

Under normal conditions, homeostatic regulation of the actions of complement proteins is mediated by specific endogenous complement inhibitor molecules (CIMs), that can be found on the surfaces of most human cells. A number of endogenous CIMs have been identified that serve to protect cells from damage mediated by complement. Pathogenic organisms and viruses are also known to produce CIMs (referred to hereinafter as "microbial CIMs") that are believed to allow the pathogens to evade destruction by the complement of their host organisms, and thus act to increase their virulence. Examples of these various types of complement inhibitor molecules are discussed below.

Endogenous CIMs, C3 Inhibitor Proteins—A family of cell-surface proteins with shared structural features has been described each of whose actions impact on C3b and are referred to as C3 inhibitor proteins.

Decay accelerating factor (DAF or CD55) exists on all cells, including red blood cells. DAF is a single chain, 70 kDa glycoprotein that is linked to the cell membrane via a glycophosphatidyinositol (GPI) moiety which inserts into the outer leaflet of the plasma membrane bilayer.

DAF regulates complement activation at the C3 convertase stage by preventing the assembly of the C3 convertases of both the classical and alternative pathways (Medof et al., 1984; Fujita et al., 1987). Thus, DAF prevents the formation of the anaphylactic cleavage fragments C3a and C5a, in addition to inhibiting amplification of the complement cascade on host cell membranes.

DAF has been shown to act exclusively in an intrinsic manner on cells, protecting only the cell on whose surface it resides while having no effect on neighboring cells. After extraction from human red blood cells, DAF reincorporates into cell membranes and is biologically active. Both membrane and secreted forms of DAF have been identified and their cDNAs have been cloned and characterized (Moran et al., 1992).

The nucleotide and amino acid sequences for human DAF are set forth in the Sequence Listings as SEQ ID NO:10.

Membrane cofactor protein (MCP or CD46) exists on all cells except red blood cells. MCP is a type I transmembrane glycoprotein that binds to C3b. MCP acts as a cofactor in the factor I-mediated cleavage of C3b and C4b deposited on self tissue. Therefore, the presence of bound MCP activates molecules that cleave C3b into inactive fragments, preventing the potentially cytolytic accumulation of C3b. Nucleotide and amino acid sequences for MCP can be found in Lublin, et al., 1988.

Complement receptor 1 (CR1 or CD35) is found on erythrocytes as well as a select group of leukocytes, including lymphocytes, neutrophils, and eosinophils. CR1 is a 190–280 kDa transmembrane protein that triggers the proteolytic degradation of membrane bound C3b molecules with which it comes in contact. It also promotes the clearance of immune complexes. Nucleotide and amino acid sequences for CR1 can be found in Wong, et al., 1985.

Factor H and C4b-binding protein each inhibit the activity of alternative pathway C3 convertase. Nucleotide and amino acid sequences for factor H can be found in Ripoche, et al., 1988; nucleotide and amino acid sequences for C4b-binding protein can be found in Chung, et al., 1985.

The genes encoding all of these endogenous C3 inhibitory proteins have been mapped to the long arm of chromosome 1, band 1q32, and constitute a locus designated the RCA (Regulators of Complement Activity) gene cluster. Notable in the molecular structure of these C3 inhibitory proteins is a common structural motif of approximately 60 amino acids designated the SCR (short consensus repeat), which is normally present in multiple copies that are not necessarily identical. See Perkins et al. 1988; Coyne, et al., 1992.

The SCR motif of these C3 inhibitory proteins has four conserved cysteine residues and conserved tryptophan, glycine, and phenylalanine/tyrosine residues. The SCRs are usually followed by a long serine/threonine rich region.

In DAF and MCP, the SCRs are known to encode functional domains necessary for full complement inhibitory activity (Adams, et al., 1991). DAF is composed of 4 SCRs juxtaposed to a serine/threonine rich region on the carboxyl terminal side of the SCRs. Most, if not all, of the functional domains are reported to reside in SCRs 2 through 4 (Coyne et al., 1992). In SEQ ID NO:10, the 4 SCRs of DAF comprise amino acid 1 through amino acid 61 (SCR 1), amino acid 62 through amino acid 125 (SCR 2), amino acid 126 through amino acid 187 (SCR 3), and amino acid 188 through amino acid 250 (SCR 4), Lublin, et al., 1989.

In addition to these endogenous C3 inhibitor proteins, pathogen C3 inhibitor proteins are also known in the art. Examples of these are discussed below under the subheading "CIMs of Pathogenic Organisms" Genetically modified C3 inhibitor proteins are also known in the art. See, for example, copending U.S. patent application Ser. No. 08/205, 508, entitled "Chimeric Complement Inhibitor Molecules, filed on Mar. 3, 1994.

Endogenous CIMs, C5b-9 Inhibitor Proteins—The archetypical C5b-9 inhibitor protein is the human glycoprotein CD59 (also known as "MACIF," "protectin," or "p18"). The nucleotide and amino acid sequences for human CD59 are set forth in the Sequence Listings as SEQ ID NO:11.

CD59 is found associated with the membranes of cells including human erythrocytes, lymphocytes, and vascular endothelial cells. It serves to prevent assembly of functional C5b-9 membrane attack complexes (MACs) and thus protects cells from complement-mediated activation and/or lysis. CD59 has an apparent molecular mass of 18–21 kilodaltons (kD) and, like DAF, is tethered to the outside of the cell membrane by a GPI anchor. See, for example, Sims et al., U.S. Pat. No. 5,135,916.

CD59 appears to function by competing with C9 for binding to C8 in the C5b-8 complex, thereby decreasing the formation of the C5b-9 membrane attack complex. (Rollins et al., 1990.) CD59 thus acts to reduce both cell activation and cell lysis by terminal complement MACs. This activity of CD59 is for the most part species-restricted; most efficiently blocking the formation of MACs under conditions where C8 and C9 are derived from homologous (i.e., human) serum. (Venneker et al., 1992.)

cDNAs encoding CD59 have been cloned and the structure of the CD59 gene has been characterized (Davies, et al., 1989; Okada, et al., 1989; Philbrick, et al., 1990; Sawada, et al., 1989; and Tone, et al., 1992). CD59 has been reported to be structurally related to the murine Ly-6 antigens (Philbrick, et al., 1990; and Petranka, et al., 1992). The genes encoding these antigens, also known as T-cell activating proteins, are members of the Ly-6 multigene family, and include Ly-6A.2, Ly-6B.2, Ly-6C.1, Ly-6C.2, and Ly-6E.1. The gene encoding the murine thymocyte B cell antigen ThB is also a member of this family (Shevach, et al. 1989; and Gumley, et al., 1992).

A distinguishing feature of the amino acid sequences of the proteins of the Ly-6 family is the arrangement of their cysteine residues. Cysteine residues of many proteins form a structural element referred to in the art as a "cysteine backbone." In those proteins in which they occur, cysteine backbones play essential roles in determining the three dimensional folding, tertiary structure, and ultimate function of the protein molecule.

The proteins of the Ly-6 multigene family, as well as several other proteins share a particular cysteine backbone structure referred to herein as the "Ly-6 motif" For example, the human urokinase plasminogen activator receptor (uPAR; Roldan, et al., 1990) and one of several squid glycoproteins of unknown function (Sgp2; Williams, et al., 1988) contain the Ly-6 motif.

Subsets of proteins having the Ly-6 motif can be identified by the presence of conserved amino acid residues immediately adjacent to the cysteine residues. Such conservation of specific amino acids within a subset of proteins can be associated with specific aspects of the folding, tertiary structure, and ultimate function of the proteins. These conserved patterns are most readily perceived by aligning the sequences of the proteins so that the cysteine residues are in register.

As discussed fully in copending U.S. patent application Ser. No. 08/105,735, filed August 11, 1993, by William L.

Fodor, Scott Rollins, Russell Rother, and Stephen P. Squinto, and entitled "Complement Inhibitor Proteins of Non-human Primates", the relevant portions of which are incorporated herein by reference, and in Rother, et al., 1994, a series of non-human primate C5b-9 inhibitory proteins have been identified which are characterized by a cysteine backbone structure which defines a specific subset of the general Ly-6 motif.

Specifically, these non-human primate CIPs include polypeptides comprising a cysteine backbone with a Ly-6 motif characterized by the formula:

$$\text{Cys-}X_2\text{-Cys-}X_{6\text{-}9}\text{-Cys-}X_5\text{-Cys-}X_6\text{-Cys-}X_{12}\text{-Cys-}X_5\text{-Cys-}X_{17}\text{-Cys-}X_0\text{-Cys-}X_4\text{-Cys.} \quad (1)$$

In addition, the non-human primate C5b-9 inhibitory proteins include amino acid sequences conforming to the following formula:

$$\text{Cys-}X_2\text{-Cys-Pro-}X_{5\text{-}8}\text{-Cys-}X_4\text{-Asn-Cys-}X_5\text{-(Thr or Ser) -Cys-}X_{11}\text{-(Gln or Arg)-Cys-}X_4\text{-(Asn or Asp)-Cys-}X_{17}\text{-Cys-}X_0\text{-Cys-}X_4\text{-Cys.} \quad (2)$$

In both formulas; the X in $X_n$ indicates a peptide containing any combination of amino acids, the n in $X_n$ represents the length in amino acid residues of the peptide, and each X at any position can be the same as or different from any other X of the same length in any other position. C5b-9 inhibitor proteins of viral origin are also known in the art, examples of which are discussed below under the subheading "CIMs of Pathogenic Organisms".

Vitronectin (S-protein) is another terminal complement inhibitor protein. A serum glycoprotein found in plasma both in native and in partially proteolyzed form, it inhibits the lytic activity of the membrane attack complex of complement, by binding to nascent C5b-7 complexes, rendering them unable to bind to C8 and C9 (Tschopp, et al., 1988).

C1 inhibitor is a plasma glycoprotein that inhibits the activity of the C1 component of the classical pathway of complement via inhibition of the proteolytic activities of the C1r and C1s subunits of C1. C1 inhibitor protein migrates in SDS gels at an apparent Mr of 104,000, but has an actual Mr of approximately 76,000. This complement and coagulation inhibitor acts by forming a peptidyl bond with a target proteinase resulting in an inactive complex (see Eldering, 1992).

CIMs of Pathogenic Organisms—Pathogens known to produce CIMs include microbial pathogens such as *Entamoeba histolytica*, which causes amebiasis; *Trypanosoma cruzi*, which causes Chagas' disease; certain strains of group A streptococci; *Salmonella choleraesuis*, various strains of which can produce a number of disease states, including enteric fever and typhoid fever; *Yersinia enterocolitica*, which causes yersiniosis; vaccinia virus; Herpes simplex virus types I and II; and *Herpesvirus saimiri*, which causes disease in monkeys (Braga, et al., 1992; Norris, et al., 1991; Hong, et al., 1990; Heffernan, et al., 1992; Bliska, et al., 1992; Isaacs, et al., 1992; McNearney; et al., 1987; Albrecht and Fleckenstein, 1992; Cooper, 1991; Gooding, 1992; and Rother, et al., 1994). It is likely that other pathogens, including non-microbial pathogens such as worms, produce as yet unidentified CIMs. In addition to those described in general terms above, examples of specific microbial CIMs are reviewed below.

Herpesvirus saimiri (HVS), a T-lymphotrophic tumor virus of New World primates, expresses various complement inhibitor molecules. CCPH is found as both a membrane glycoprotein (mCCPH) and a secreted derivative (sCCPH).

As discussed fully in copending PCT application Serial No. PCT/US 93/00672, filed Jan. 12, 1993, by Bernhard Fleckenstein and Jens-Christian Albrecht, and entitled "Complement Regulatory Proteins of Herpesvirus Saimiri", the relevant portions of which are incorporated herein by reference; and in Rother, et al., 1994; a protein of the herpesvirus saimiri having C5b-9 inhibitory activity has been discovered (referred to herein as "HVS-15"). This viral protein has the Ly-6 motif which is characteristic of the non-human primate C5b-9 inhibitory proteins discussed above, i.e., its structure is described by formulas (1) and (2) above.

Herpesvirus Saimiri also expresses a C3 inhibitor protein referred to as CCPH. The structural layout of CCPH is similar to those of CD55 and CD46 and comprises SCR domains. CCPH is found as both a membrane glycoprotein (mCCPH) and a secreted derivative (sCCPH). See, for example, Albrecht, et al., 1992. The nucleotide and amino acid sequences for mCCPH and sCCPH are set forth in the Sequence Listings as SEQ ID NO:12 and SEQ ID NO:13, respectively.

The vaccinia virus complement inhibitor protein VCP has been shown to prevent antibody-dependent complement enhanced neutralization of infectivity and to contribute to viral virulence (Isaacs, et al., 1992).

Herpes simplex virus glycoproteins gC-1 and gC-2 have been shown to inactivate complement component C3b, and the presence of either of these glycoproteins in virions has been shown to provide protection against complement-mediated neutralization of viral infectivity (McNearney, et al., 1987).

The M protein of group A streptococci is a factor that has been shown to be required for bacterial virulence, and has also been shown to inhibit alternative C3 convertase and classical C5 convertase, two important enzymatic activities needed for the formation of active terminal complement components (Hong, et al., 1990).

The TraT protein of *Escherichia coli* has been shown to be the determinant of the serum resistance conferred by the *E. coli* R factor, which enhances the virulence of this bacterium (Pramoonjago, et al., 1992).

The rck gene of *Salmonella choleraesuis* serotype typhimurium (also known as *Salmonella typhimurium*) has been shown to be the determinant of the serum resistance conferred by the Salmonella virulence plasmid (Heffernan, et al., 1992).

Other CIMs—In addition to these endogenous and microbial CIMs, a number of other proteins are known that can inhibit the complement system.

Cobra venom factor (CoVF or CVF) is a C3b-like molecule found in cobra venom that is resistant to C3b inactivating factors (Leventhal, et al., 1993). This C3b analog combines with components of the alternative complement pathway to form a highly stable enzyme complex which exhibits high levels of C3 convertase activity and causes massive consumption of C3, terminal complement components, and other factors. This activity results in the depletion of complement components and the consequent exhaustion of the complement cascade. The end result of CVF action in a body fluid is thus to block terminal complement activity until more complement components make their way into the complement depleted body fluid.

Antibodies reactive with complement components have the potential to block complement component action and thereby to inhibit complement activity. Such complement inhibitory blocking antibodies include the monoclonal antibodies against human C5b-9 proteins discussed in U.S. Pat.

No. 5,135,916, issued Aug. 4, 1992. In addition to native antibodies, antigen binding fragments (e.g., Fab' preparations) of such immunoglobulins, as well as recombinantly expressed antigen binding proteins, including immunoglobulins, chimeric immunoglobulins, "humanized" immunoglobulins, antigen binding fragments of such immunoglobulins, single chain antibodies, and other recombinant proteins containing antigen binding domains derived from immunoglobulins, all of which can be prepared by methods well known in the art, can be used as CIMs.

Various non-protein CIMs are also known in the art. See copending U.S. patent application Ser. No. 08/278,550, entitled "Retroviral Transduction of Cells Using Soluble Complement Inhibitors", which is being filed concurrently herewith in the names of Russell P. Rother, Scott A. Rollins, James M. Mason, and Stephen P. Squinto.

SUMMARY OF THE INVENTION

In view of the foregoing state of the art, it is an object of the present invention to facilitate the use of RVVPs to efficiently transduce the cells of a primate patient, e.g., a human patient, upon administration of the RVVPs to cells in contact with the body fluids of the patient. Since the RVVPs of the invention and those used in the practice of the invention are generally used to effect gene therapy, such RVVPs preferably contain an exogenous gene operably linked to a promoter effecting the expression of the gene and operably linked to a portion of the vector which recombines with DNA in the genome of the patient.

It is an additional object of the present invention to provide pharmaceutical agents for gene therapy in primates, and to provide articles of manufacture containing such agents.

In order to achieve these an other objects, the invention provides modified retroviral vector particles and modified retrovital producer cells producing such particles. The modifications involved in making such particles and cells comprise genetic alterations to effect the expression by these cells and particles of complement inhibitor activity. The genetic alterations comprise the introduction of nucleic acid expression constructs directing the expression of retroviral SU (gp70)/complement inhibitor chimeric proteins into cells from which the producer cells are derived.

The invention thus provides Retroviral vector particles expressing a complement inhibitor activity. The complement inhibitor activity expressed by the retroviral vector particle is a DAF activity, a CCPH activity, a CD59 activity, or an activity provided by another complement inhibitor molecule.

The invention also provides methods for transducing a cell in the presence of a body fluid with a retroviral vector particle comprising administering the retroviral vector particle of the invention to a target cell. In a preferred embodiment, the target cell is in contact with a body fluid. In a further preferred embodiment, the body fluid is a heparin decoagulated bone marrow aspirate diluted in tissue culture medium. In another preferred embodiment the body fluid is selected from the group consisting of blood, plasma, or serum.

The invention also provides pharmaceutical preparations comprising a retroviral vector particle expressing a complement inhibitor activity in a solution suitable for injection, e.g., intravenous injection. In accordance with the invention, such pharmaceutical preparations may be distributed in the form of an article of manufacture comprising the pharmaceutical preparation and a label indicating that the pharmaceutical preparation is to be used to provide gene therapy to a patient.

BRIEF DESCRIPTION OF THE DRAWINGS

FIG. 1 shows results obtained using human serum and LXSN RVVPs prepared in the LXSN/DAF, LXSN/CCPH, and LXSN/CD59 clones that produced the most resistant RVVPs for each chimeric gp70 type tested. Also shown for comparison are results obtained with a DAF clone, LXSN3/DAF34, producing less resistant RVVPs which were also tested in experiments using whole blood.

FIG. 2 shows results obtained using human whole blood and LXSN RVVPs prepared in packaging cells of clone LXSN3/DAF34.

Figure 1:
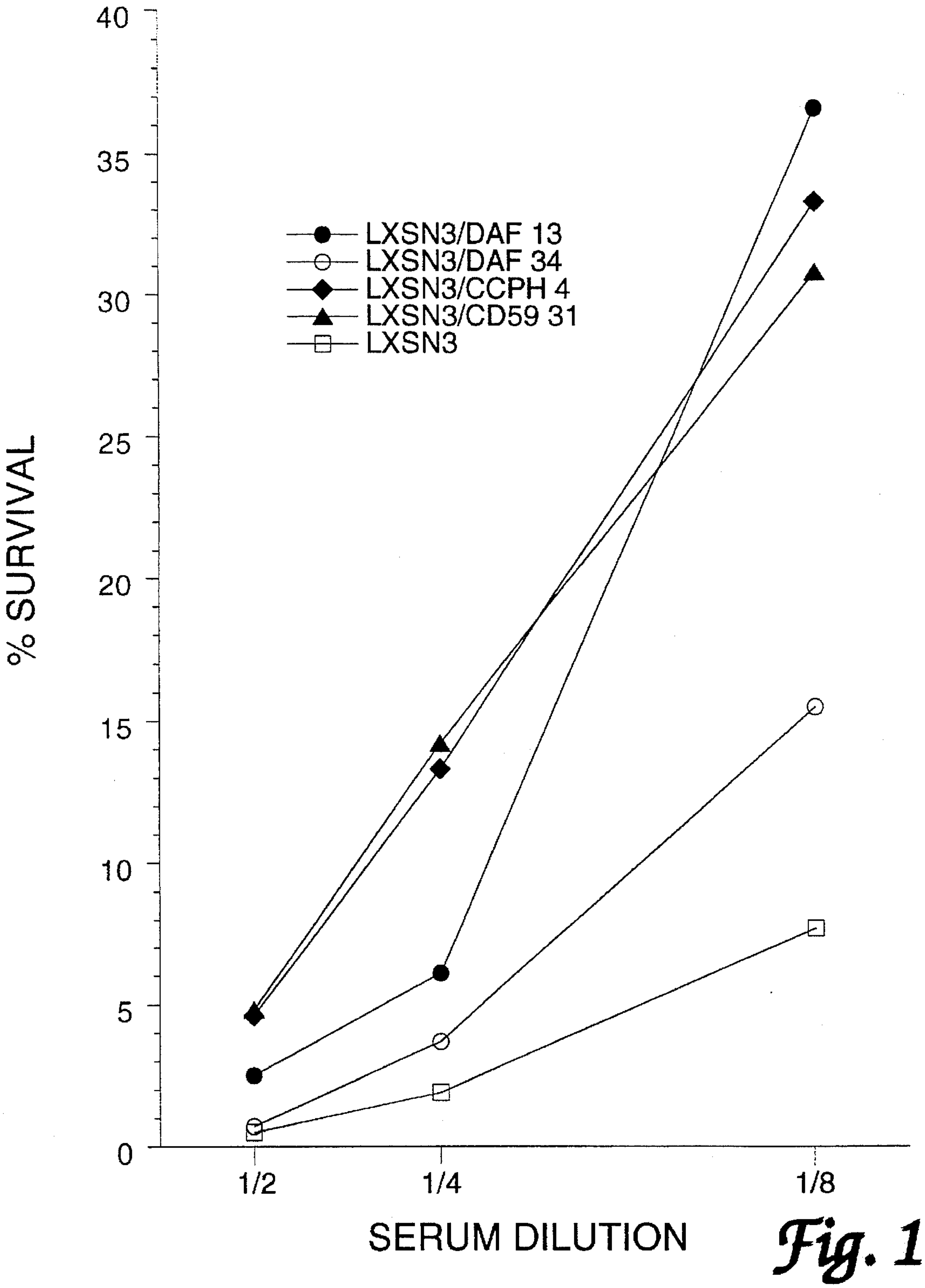
FIGS. 1 and 2 illustrate the protection of RVVPs by envelope/CIM fusion proteins. RVVP inactivation by human serum or human whole blood was measured using conventional LXSN RVVPs (as controls) and LXSN RVVPs prepared in packaging cells expressing examples of the envelope/CIM fusion proteins of the invention.

The foregoing drawings, which are incorporated in and constitute part of the specification, illustrate certain embodiments of the invention, and together with the description, serve to explain the principles of the invention. It is to be understood, of course, that both the drawings and the description are explanatory only and are not restrictive of the invention.

DETAILED DESCRIPTION OF THE INVENTION

The present invention relates to gene therapy using retroviral vector particles.

I. Retroviral Vector Particles and Packaging Cells for Making Such Particles General discussions of packaging cells, retroviral vector particles and gene transfer using such particles can be found in various publications including PCT Patent Publication No. WO 92/07943, EPO Patent Publication No. 178,220, U.S. Pat. No. 4,405,712, Gilboa, 1986; Mann, et al., 1983; Cone and Mulligan, 1984; Eglitis, et al., 1988; Miller, et al., 1989; Morgenstern and Land, 1990; Eglitis, 1991; Miller, 1992; Mulligan, 1993, and Ausubel, et al., 1992.

The packaging cells of the invention are produced by 1) constructing one or more expression vectors comprising recombinant nucleic acid molecules encoding the retroviral pol, env, and gag proteins (hereinafter referred to as "packaging vectors"); 2) constructing a chimeric vector directing the expression of a chimeric SU(gp70)/CIM protein; 3) introducing the one or more packaging vectors and the chimeric vector into cultured cells, typically, mammalian cells; and 4) obtaining the desired packaging cells by selecting those cells of the culture which stably express proteins encoded by the one or more packaging vectors and the chimeric vector.

The manipulation of retroviral nucleic acids to construct packaging vectors and packaging cells is accomplished using techniques known in the art. See Ausubel, et al., Volume 1, Section III (units 9.10.1–9.14.3), 1992; Sambrook, et al., 1989; Miller, et al., 1989; Eglitis, et al., 1988; U.S. Pat. Nos. 4,650,764, 4,861,719, 4,980,289, 5,122,767, and 5,124,263; as well as PCT Patent Publications Nos. WO 85/05629, WO 89/07150, WO 90/02797, WO 90/02806, WO 90/13641, WO 92/05266, WO 92/07943, WO 92/14829, and WO 93/14188.

These manipulations typically involve the use of DNA copies of the gag, pol, and env retroviral genes cloned in plasmid vectors. Such plasmid vectors containing retroviral genes can be prepared by, for example, isolation of DNA copies of the viral genome from the cytoplasm of infected cells (using, for example, the method of Hirt, 1967), restriction digestion of the DNA copies of the viral genome (or PCR amplification of regions of interest of the DNA, generally followed by restriction digestion of the PCR product) to produce desired fragments, and multiple rounds of subcloning of the fragments, along with fragments containing suitable selectable marker and origin of replication sequences, to produce operable packaging vectors.

Multiple rounds of subcloning are used because it has been found that the typical bacterial cells used as plasmid hosts in subcloning, e.g., *E. coli*, tend to create deletions in the nucleotide sequences of newly inserted retroviral insert fragments when such fragments comprise more than about 4 kbp. Accordingly, construction of the final packaging vector proceeds more efficiently if small retroviral insert fragments (on the order of less than about 4 kbp) are sequentially assembled in the plasmid through multiple rounds of subcloning.

To form the packaging cells, the packaging vector or vectors and the chimeric vector are introduced into suitable host cells. Examples of such cells are found in, for example, Miller and Buttimore, *Mol. Cell Biol.*, 6:2895–2902, 1986; Markowitz, et al., *J. Virol.*, 62:1120–1124, 1988; Cosset, et al., *J. Virol.*, 64:1070–1078, 1990; U.S. Pat. Nos. 4,650,764, 4,861,719, 4,980,289, 5,122,767, and 5,124,263, and PCT Patent Publications Nos. WO 85/05629, WO 89/07150, WO 90/02797, WO 90/02806, WO 90/13641, WO 92/05266, WO 92/07943, WO 92/14829, and WO 93/14188. Preferred host cells are from the NIH/3T3 mouse embryo fibroblast line, e.g. ATCC CRL 1658 cells, or the mouse embryo fibroblast cell line PA317, ATCC CRL 9078.

Once a packaging cell line has been established, the next step is to generate "producer cells" by introducing retroviral vectors into the packaging cells. Examples of such retroviral vectors are found in, for example, Korman, et al., 1987, *Proc. Natl. Acad. Sci. USA*, 84:2150–2154; Miller and Rosman, *Biotechniques*, 7:980–990, 1989; Morgenstern and Land, 1990; U.S. Pat. Nos. 4,405,712, 4,980,289, and 5,112,767; and PCT Patent Publications Nos. WO 85/05629, WO 90/02797, and WO 92/07943. The retroviral vector includes a psi site and one or more exogenous nucleic acid sequences selected to perform a desired function, e.g., an experimental, diagnostic, or therapeutic function. These exogenous nucleic acid sequences are flanked by LTR sequences which function to direct high efficiency integration of the sequences into the genome of the ultimate target cell.

II. Gene Transfer for Gene Therapy

The many applications of gene therapy are well known and have been extensively reviewed (see, for example, Boggs, 1990; Kohn, et al., 1989; Lehn, 1990, Verma, 1990; Weatherall, 1991; and Felgner and Rhodes, 1991).

A variety of genes and DNA fragments can be incorporated into RVVPs, including the RVVPs of the invention, for use in gene therapy. These DNA fragments and genes may direct the expression of RNA and/or protein molecules that render them useful as therapeutic agents. Protein encoding genes of use in gene therapy include those encoding various hormones, growth factors, enzymes, lymphokines, cytokines, receptors, and the like.

Among the genes that can be transferred in accordance with the invention are those encoding polypeptides that are absent, are produced in diminished quantities, or are produced in mutant form in individuals suffering from a genetic disease. Other genes of interest are those that encode proteins that, when expressed by a cell, can adapt the cell to grow under conditions where the unmodified cell would be unable to survive, or would become infected by a pathogen. Genes that target transduced cells for destruction are useful for the treatment of neoplasias. Genes encoding proteins that have been engineered to circumvent a metabolic defect are also suitable for transfer into the cells of a patient using the methods and compositions of the present invention. Such genes include the transmembrane form of CD59 discussed in copending U.S. patent application Ser. No. 08/205,720, filed Mar. 3, 1994, entitled "Terminal Complement Inhibitor Fusion Genes and Proteins" and copending U.S. patent application Ser. No. 08/206,189, filed Mar. 3, 1994, entitled "Method for the Treatment of Paroxysmal Nocturnal Hemoglobinuria".

In addition to protein-encoding genes, the present invention can be used to introduce nucleic acid sequences directing the expression of medically useful RNA molecules into cells. Examples of such RNA molecules include anti-sense molecules and catalytic molecules, such as ribozymes.

In order to expedite rapid transduction by eliminating the need to wait for target cells to divide, and to allow transduction of cells that divide slowly or not at all, the use of retroviral transduction systems producing RVVPs that can transduce non-dividing cells may be preferred. Such transduction systems are disclosed in copending U.S. patent applications Ser. Nos. 08/181,335 and 08/182,612, both entitled "Retroviral Vector Particles for Transducing Non-Proliferating Cells" and both filed Jan. 14, 1994.

III. Preparation and Administration of Complement Resistant RVVPs.

The present invention provides new RVVPs for administration to the body fluids of a patient. Significantly, the present invention allows for the use of more practical protocols for RVVP administration. It does so by eliminating the need to remove the target cells from body fluids prior to administration of the RVVPs. Specifically, in accordance with the invention, engineered RVVPs are administered to cells while those cells are in contact with body fluids such as blood, plasma, serum, lymph, the fluids making up bone marrow, and the like.

As discussed above, oncoretroviruses have an envelope SU protein that contains a receptor binding region. Applicants have found that RVVPs derived from oncoretroviruses can be made resistant to inactivation by complement in the body fluids of a patient if the receptor binding region of the retrovirus SU protein, which may be amphotropic, ecotropic, polytropic, or xenotropic, among other types, is modified such that at least a portion of the receptor binding region of the envelope protein is removed and replaced with a complement inhibitor molecule. Thus, there is provided a retroviral packaging vector (chimeric vector) wherein at least a portion of the polynucleotide segment which encodes the receptor binding region of the envelope protein of the retrovirus has been deleted and replaced with a polynucleotide segment encoding a complement inhibitor protein.

In the preferred embodiments, the retrovirus from which the RVVPs of the invention are derived is a murine leukemia virus, with the Moloney murine leukemia virus being most preferred. In accordance with the invention, such RVVPs can be made resistant to inactivation by complement if a portion of the SU protein is deleted and replaced with a complement inhibitor molecule.

In general, a retroviral SU protein includes the following regions: (i) the secretory signal or "leader" sequence; (ii) the receptor binding domain; (iii) the hinge or neck region; and (iv) the body portion. Preferably, at least a portion of the polynucleotide segment encoding the receptor binding domain of the SU protein is deleted and replaced with a polynucleotide segment encoding a complement inhibitor molecule. More preferably, a polynucleotide segment encoding the entire receptor binding domain of the SU protein is deleted and replaced with a polynucleotide segment encoding a complement inhibitor molecule. In another embodiment, a polynucleotide segment encoding the entire receptor binding domain of the SU protein, plus all or a portion of the DNA (RNA) encoding the hinge region of the SU protein is deleted and replaced with a polynucleotide segment encoding a complement inhibitor protein.

The SU protein may be derived from an ecotropic murine leukemia virus, a xenotropic murine leukemia virus, an amphotropic murine leukemia virus, or a oncoretrovirus infecting a non-murine species such as the gibbon ape leukemia virus. The mature ecotropic gp70 (eco gp70) protein has 469 amino acids (SEQ ID NO:7). Amino acid residues 1–33 constitute the leader sequence; amino acid residues 34–263 constitute the receptor binding domain; amino acid residues 264–312 constitute the hinge region; and amino acid residues 313–469 constitute the body portion. Preferably, a polynucleotide segment encoding some or all of amino acid residues 34 to 263 (i.e., the receptor binding domain) is removed and replaced with a polynucleotide segment encoding a complement inhibitor protein.

Xenotropic gp70 (xeno gp70) protein has 443 amino acid residues (SEQ ID NO:8). Amino acid residues 1–30 constitute the leader sequence; amino acid residues 31–232 constitute the receptor binding domain; amino acid residues 233–286 constitute the hinge (or neck) region; and amino acid residues 287–443 constitute the body portion. Preferably, a polynucleotide segment encoding some or all of amino acid residues 31 to 232 is removed and replaced with a polynucleotide segment encoding a complement inhibitor protein.

Nucleic acid molecules encoding a variety of CIMs can be used to protect RVVPs from complement attack. Those CIMs include the molecules discussed above under the heading "Inhibitors of the Complement System". Preferred CIMs are DAF, CCPH, and CD59.

The CIMs can be used to protect a variety of RVVPs. Preferred RVVPs are those suitable for gene therapy, including the LXSN particles discussed below in the examples. The RVVPs will include a gene or other nucleic acid sequence whose transfer is desired.

In accordance with the invention in certain of its aspects, RVVPs are prepared using producer cells which contain plasmids encoding fusion proteins containing viral envelope and CIM sequences. Such RVVPs, when so prepared, express the activities of at least one CIM and thus are resistant to inactivation by complement. RVVPs that are less sensitive to inactivation by complement as a result of genetic engineering of cells from which producer cells are derived are referred to herein as complement resistant RVVPs or crRVVPs.

In general, to form packaging cells in accordance with the invention, the plasmid or plasmids encoding the chimeric SU(gp70)/CIM fusion proteins of the invention are introduced into host cells, either before or after the introduction of the packaging vector or vectors described above. The producer cells of the invention are prepared by the introduction of a retroviral vector into the packaging cells of the invention.

The producer cells of the invention are used to produce crRVVPs by culturing of the cells in a suitable growth medium. If desired, the particles can be harvested from the culture and administered to the target cells which are to be transduced, or the producer cells can be grown together with the target cells. The growth of producer cells together with target cells can be accomplished by co-culture of the cells in vitro, or, when desired, the producer cells are co-cultured together with the target cells by implantation of the producer cells in the patient.

In particular, gene therapy may be carried out by a procedure in which a retroviral producer cell (i.e., an engineered cell producing crRVVPs) is implanted into the body of the patient to be treated. This may be a particularly desirable procedure in the treatment of certain cancers. Recent in vivo studies have demonstrated that procedures involving the implantation of producer cells into rat solid tumors can effectively deliver RVVPs to adjacent cells (Culver et al., 1992). In one variation of such procedures, producer cells are engineered to express the herpes simplex virus thymidine kinase (HSVTK) gene. Treatment of a patient with ganciclovir post-implantation will kill the HSVTK expressing producer cells as well as any immediately surrounding cells, which, in such procedures, will be tumor cells.

In related studies, producer cells injected into the brain of rats or monkeys were shown to survive for approximately 15 days without proliferating (Ram et al., 1993). The survival of xenogeneic producer cells in the primate brain is not surprising considering that the brain is an immunoprivileged site relative to complement activity (Widner and Brundin, 1988) and therefore, hyperacute rejection (HAR) commonly associated with xenotransplants into primates is less likely to occur in the brain. HAR of xenografts in primates normally occurs within minutes of transplantation due to the activation of the classical complement pathway by preexisting antibodies to alpha-galactosyl epitopes found on the surface of mammalian cells excluding man, apes and Old World monkeys (Galili et al., 1987; and Neethling et al., 1994).

Accordingly, when implantation is performed, the producer cells may be of the type described in copending U.S. patent application Ser. No. 08/278,282, entitled "Methods for Reducing Hyperacute Rejection of Xenografts", which is being filed concurrently herewith in the names of Mauro S. Sandrin, William L. Fodor, Russell P. Rother, Stephen P. Squinto, and Ian F. C. McKenzie. They also may be of the type described in copending U.S. patent application Ser. No. 08/278,639, entitled "Retrovital Transduction of Cells in the Presence of Complement", which is being filed concurrently herewith in the names of Russell P. Rother, Scott A. Rollins, William L. Fodor, and Stephen P. Squinto.

The crRVVPs of the invention are substantially protected from inactivation upon exposure to the body fluids of an organism of the patient's species, e.g. incubation in whole blood or in 40% serum. An at least 5% reduction will, in general, comprise a "substantial reduction". Smaller reductions are also considered "substantial" if they represent a statistically significant reduction; i.e., a reduction that, when obtained in replicate assays and analyzed by a conventional statistical test, such as the student's T test, will give a probability value, p, which is less than or equal to 0.05, and, preferably, less than or equal to 0.015.

The substantial nature of such apparently small reductions is due to the huge numbers of RVVPs that can be prepared using conventional methods. RVVP titers of greater than $10^9$ RVVPs per ml can be prepared by concentration (e.g., by tangential flow filter concentration) of RVVP containing supernatants obtained using retroviral transduction systems known in the art.

As an example, a 100% inactivation may be obtained in the presence of a body fluid, and a 1% reduction in RVVP inactivation may be achieved using a crRVVP, compared to an unprotected RVVP, i.e., an RVVP not engineered to express the activity of a CIM. In such a case, if 1 ml of a $10^9$ RVVP per ml preparation is administered to the body fluid, no RVVPs will be present when unprotected RVVPs are administered, and ten million RVVPs will be present in the body fluid when the RVVPs of the invention are administered.

The crRVVPs of the invention can be used for ex vivo gene therapy in accordance with various techniques known in the art. In general terms, these techniques involve the removal of target cells of interest from a patient, incubation of the target cells with the retroviral vector particles, and reintroduction of the transduced target cells into the patient. Various procedures can be applied to the target cells while they are in the ex vivo state, including selection of subsets of the target cells prior to transduction, isolation of transduced cells, selection of subsets of isolated, transduced cells, propagation of target cells either before or after transduction, in cases where the cells are capable of proliferation, and the like.

Delivery of nucleic acid molecules of interest may also be accomplished ex vivo or in vivo by administration of the retroviral vector particles of the invention to a patient. In particular, in accordance with the invention, the crRVVPs can be administered to the target cells while the cells are bathed in body fluids. Specifically, the crRVVPs may be administered to the target cells via administration to the body fluids bathing cells in the ex vivo unwashed state using otherwise conventional protocols for ex vivo transduction of target cells, or may be administered to body fluids in vivo. In such in vivo applications, the injection of crRVVPs directly into solid tissues is considered to be administration to body fluids, as the cells in solid tissues are bathed in interstitial fluids, and the crRVVPs enter the target cells following mixture with such fluids.

In connection with such in vivo or ex vivo administration, retroviral vector particles can be pre-treated in accordance with the procedures discussed in co-pending application Ser. No. 08/098,944, filed Jul. 28, 1993, in the name of James M. Mason and entitled "Pre-binding of Retroviral Vector Particles with Complement Components to Enable The Performance of Human Gene Therapy In Vivo." Also, the procedures described in copending U.S. patent application Ser. No. 08/278,550, entitled "Retroviral Transduction of Cells Using Soluble Complement Inhibitors", which is being filed concurrently herewith in the names of Russell P. Rother, Scott A. Rollins, James M. Mason, and Stephen P. Squinto and in copending U.S. patent application Ser. No. 08/278,639, entitled "Retroviral Transduction of Cells in the Presence of Complement", which is being filed concurrently herewith in the names of Russell P. Rother, Scott A. Rollins, William L. Fodor, and Stephen P. Squinto can be used in connection with such administration.

The administration of the crRVVPs can be performed locally, e.g., by aerosol, transmucosal, or transdermal delivery, or, more typically, by a systemic route, e.g., orally, intravenously, intraperitoneally, intramuscularly, transdermally, intradermally, subdermally, transmucosally, or intrathecally. For systemic administration, injection is preferred.

IV. Pharmaceutical Compositions

The crRVVPs of the invention can be formulated as pharmaceutical compositions. Such compositions will generally include a pharmaceutically effective carrier, such as saline, buffered (e.g., phosphate buffered) saline, Hank's balanced salts solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. See, for example, *Remington's Pharmaceutical Sciences*, Mack Publishing Company, Philadelphia, Pa., 17th ed., 1985.

The pharmaceutical compositions are suitable for use in a variety of drug delivery systems. Langer, *Science*, 249:1527–1533, 1990, reviews various drug delivery methods currently in use. In some cases, the drug delivery system will be designed to optimize the biodistribution and/or pharmacokinetics of the delivery of the retroviral vector particles. See, for example, *Remington's Pharmaceutical Sciences*, supra, Chapters 37–39. For example, the particles can be incorporated in vesicles composed of substances such as proteins, lipids (for example, liposomes), carbohydrates, or synthetic polymers. See, for example, Langer, 1990, supra.

In certain preferred embodiments, the invention also provides articles of manufacture consisting of pharmaceutical compositions that contain (a) crRVVPs and/or producer cells, and (b) packaging material indicating that the pharmaceutical composition is to be used to effect gene therapy.

The pharmaceutical compositions of the invention can be administered in a variety of unit dosage forms. The dose will vary according to, e.g., the particular crRVVP or producer cell, the manner of administration, the particular disease being treated and its severity, the overall health and condition and age of the patient, and the judgment of the prescribing physician. Dosage levels for human subjects are generally between about $10^6$ and $10^{14}$ colony forming units of retroviral vector particles per patient per treatment. Producer cells are administered in sufficient numbers to produce therapeutic levels of crRVVPs, e.g., at least about $10^3$–$10^4$ producer cells.

In terms of clinical practice, the compositions and methods of the present invention will have broad therapeutic utility in facilitating the treatment of a wide range of inherited and acquired diseases and medical conditions including, without limitation, hematologic diseases, cardiopulmonary diseases, endocrinological diseases, immunological diseases, neoplasias, and the like.

Without intending to limit it in any manner, the present invention will be more fully described by the following examples.

MATERIALS AND METHODS

DNA molecules encoding three different complement inhibitor molecules were each fused with DNA molecules encoding the MoMLV ecotropic gp70 molecule of plasmid pCee (Muenchau et al., 1992) to engineer chimeric DNA molecules encoding chimeric proteins. Each fusion was designed so that the N-terminal region containing the receptor binding domain of gp70 was removed and replaced with a complement inhibitor sequence. These chimeric DNA molecules were constructed in vectors designed for expression in mammalian cells. Once generated, the chimeric complement inhibitor/gp70 expression vectors were co-transfected into the GPE86-LXSN3 producer cell line (see below) with plasmid pTH at a 50 to 1 ratio. Plasmid pTH (TH stands for TK-hygro) was derived from plasmid p291 (Yates et al., 1985) by digestion of p291 with EcoRV and SspI, purification of the resulting Hph containing fragment, and self ligation of the purified fragment. The resulting plasmid contains sequences encoding the hygromycin resistance gene Hph, expression of which is driven by a TK (thymidine kinase) promoter.

Transfectants were selected for approximately 2 weeks in D10 medium (see below) containing 150–200 μg/ml of active hygromycin B. Clones were isolated using cloning rings and vector particles generated from expanded clones were assayed for complement resistance.

Construction of the CCPH/gp70E fusion. Plasmid pCDNAI-Amp-Flag-CCPH was prepared as follows. An mCCPH encoding cDNA fragment was directionally subcloned into the mammalian expression vector, pcDNAI-AMP (Invitrogen Corporation, San Diego, Calif.) as an EcoRI and NotI restriction fragment of the mCCPH subclone, pHVS-A11-mCCPH (also referred to as pKS-/mCCPH, ATCC #69178). A 5' FLAG tagged version of mCCPH incorporating a CD59 leader peptide encoding sequence was constructed by the following steps. A 5' FLAG/mCCPH DNA fragment was prepared utilizing the EcoRI/NotI restriction fragment of pKS/mCCPH (described above) as template in a polymerase chain reaction (PCR). The 5' primer for the PCR was 5' GCCGGCCTGC AGGACTACAA AGACGATGAC GATAAA TTAA GCTGTCCTAC ACGTAACCAG-3' (SEQ ID NO:1), where the underlined sequences represent a unique PstI site that was used for cloning purposes and where the italicized type indicates the FLAG epitope encoding sequence. The 3' primer for the PCR was 5'-CTTCCATTTA AAAGATCTTG CGG-3' (SEQ ID NO: 2), where the underlined sequence represents a unique BglII site used for cloning purposes that corresponds to a BglII site located within CCPH. The 5'FLAG mCCPH DNA fragment generated in this PCR was cloned into the pCRII vector (Invitrogen Corporation, San Diego, Calif.) and sequenced to confirm that the fragment contained the sequence set forth in SEQ ID NO: 3. A CD59 leader-FLAG-mCCPH clone was then constructed by digesting the mCCPH-pcDNAI-Amp plasmid with BamHI and BglII and purifying the resulting approximately 5870 bp fragment containing the bulk of the mCCPH-pcDNAI-Amp plasmid separate from the approximately 250 bp fragment containing native 5' coding sequences of mCCPH. Subsequently, the 5'FLAG mCCPH fragment and the human CD59 leader cDNA fragment (BamHI-PstI) were directionally cloned in a three fragment ligation reaction with the purified approximately 5870 bp BamHI-BglII CCPH fragment. Competent *E. coli* cells were transformed with the ligation product, miniprep plasmid DNAs were prepared, and a plasmid containing the desired construction (i.e., a 5' FLAG tagged version of mCCPH incorporating a CD59 leader peptide encoding sequence) was identified by gel analysis of restriction digests and designated pCDNAI-Amp-Flag-CCPH.

Plasmid pCDNAI-Amp-Flag-CCPH was double digested with NdeI and EcoRV, and an approximately 1300 bp fragment isolated and ligated to a fragment of pCee that was prepared as follows. Plasmid pCee (Muenchau et al., 1992) was digested with AccI and the ends were filled in using the Klenow fragment of DNA polymerase I and nucleotide triphosphates. The DNA was then digested with NdeI and electrophoresed, and a resulting approximately 4500 bp fragment, was isolated from the agarose gel. Competent *E. coli* cells were transformed with the product of the ligation of the pCDNAI-Amp-Flag-CCPH fragment and the pCee fragment, miniprep plasmid DNAs were prepared, and appropriate plasmids (i.e., those containing the Flag-CD59 leader-CCPH-gp70 fusion construction) were identified by gel analysis of restriction digests. The CCPH/gp70 junction of an appropriate plasmid was sequenced to confirm that it included the sequence set forth in SEQ ID NO: 4, demonstrating that an in frame gene fusion of CCPH with gp70 had indeed been created. This plasmid, CCPH/gp70E, has been deposited with the ATCC and given the designation 69650.

CD59/gp70E Plasmid Construction. Plasmid pCDGPI#1-pCDNAI-Amp (ATCC #69564) (see copending U.S. patent application Ser. No. 08/205,508, entitled "Chimeric Complement Inhibitor Molecules, filed on Mar. 3, 1994) was digested with EagI. Ends were partially filled with the Klenow fragment of DNA polymerase I and only dGTP. The DNA was then digested with NdeI and an approximately 780 bp CD59 fragment was isolated. Plasmid pCee was digested with BspEI and its ends were filled with the Klenow fragment of DNA polymerase I and only dCTP. The plasmid DNA was then digested with NdeI and an approximately 4750 bp pCee NdeI/BspEI partial fill fragment was isolated. This fragment was then ligated with the approximately 780 bp CD59 fragment. Competent *E. coli.* cells were transformed with the ligation product, miniprep plasmid DNAs were prepared, and appropriate plasmids (i.e., those containing the desired construction) were identified by gel analysis of restriction digests. The CD59/gp70 junction of an appropriate plasmid was sequenced to confirm that it included the sequence set forth in SEQ ID NO: 5, demonstrating that an in frame gene fusion had indeed been created. This plasmid, CD59/gp70E, has been deposited with the ATCC and given the designation 69652.

DAF/gp70E Plasmid Construction. Plasmid pDC#1-pCDNAI-Amp (ATCC #69563) (see copending U.S. patent application Ser. No. 08/205,508, entitled "Chimeric Complement Inhibitor Molecules, filed on Mar. 3, 1994) was double digested with NdeI and BsmI. An approximately 1110 bp fragment was isolated. This 1110 bp NdeI/BsmI fragment contains sequences encoding DAF. Plasmid pCee was digested with PflM1 and treated with a ten fold excess of calf intestinal phosphatase (CIP, New England Biolabs, Beverly, Mass.) to allow the contaminating exonuclease activity present in commercial preparations of calf intestinal phosphatase to remove the 3' hydroxyl guanine nucleotide. The CIP treated DNA was then digested with NdeI and the resulting approximately 4600 bp fragment was isolated and ligated to the approximately 1110 bp NdeI/BsmI fragment. Competent *E. coli* cells were transformed with the ligation product, miniprep plasmid DNAs were prepared, and appropriate plasmids (i.e., those containing the DAF gp70 construction) were identified by gel analysis of restriction digests. The DAF/gp70 junction of an appropriate plasmid was sequenced to confirm that it included the sequence set forth in SEQ ID NO: 6, demonstrating that an in frame gene fusion had indeed been created. This plasmid, DAF/gp70E, has been deposited with the ATCC and given the designation 69651.

Transfection and Expression of CIM/gp70E Chimeras. The producer cell line GPE86-LXSN3 was generated by transducing GPE86 packaging cells (Markowitz et al., 1988) with vector particles bearing retroviral vector LXSN sequences (Miller and Rosman, 1989) and selecting for neomycin resistance and high titer. Colonies were cloned out, and GPE86-LXSN clone #3 having a NeoR titer of approximately $2\times10^6$ CFU/ml was chosen for further use.

GPE86-LXSN3 producer cells were co-transfected with a 50 to 1 ratio by mass of CIM/gp70E and plasmid pTH, described above.

Approximately 30 colonies were cloned out and expanded for each CIM/gp70E construct. Vector particle supernatants, less than 24 hours old, were collected and stored at −70° C. until assayed for complement resistance.

Vector Particles, Blood and Sera. Vector particles which had been stored frozen at −70° C. were thawed at 37° C. and used in the complement resistance titer assay. Human blood was drawn from healthy volunteers in the presence of 25 units/ml heparin to prevent clotting. Human serum was obtained from Sigma Chemical Company, St. Louis, Mo. Human serum was also obtained from healthy donors and prepared as described in Welsh et al., 1976.

Complement Resistance Titer Assay. Generally, 100 μl of thawed vector particle supernatant was mixed with an equal volume of heat inactivated (56° C. for 30 minutes) or active complement containing human serum (undiluted or diluted in PBS supplemented with 0.15 mM $CaCl_2$ and 0.5 mM $MgCl_2$). This mixture was then incubated at 37° C. for 30 to 60 minutes to allow complement to act upon the vector particles. 100 μl of the vector particle/serum mixture was then titered by analyzing transduction of NIH/3T3 cells using G418 resistance as a marker as described below. Experiments with whole human blood were performed similarly except that, after the 30 to 60 minute incubation at 37° C., samples were centrifuged at 3000×g for 10 minutes at 4° C. prior to transduction of NIH 3T3 cells.

Serial dilutions of RVVP samples were assayed for titer of transducing RVVPs on NIH/3T3 cells (ATCC designation CCL 163). $2.5\times10^4$ cells were plated in 2 ml of DMEM containing 10% FBS (referred to herein as D10) in wells of 6-well plates. The following day, medium in each well was replaced with 2 ml of D10 containing 8 mg/ml of polybrene. The RVVP sample was then added. Ten-fold or 100-fold serial dilutions were made from the original well and added to adjacent wells. The plates were then incubated for 24 hours. Medium was then once again replaced with 2 ml of the D10, in this case containing 500 mg/ml of G418 (active).

Selection was accomplished by incubation in the G418 containing D10 for 7–12 days with 2 changes of medium during this period. Following this selection, medium was removed and surviving colonies were fixed and stained for 15 minutes with a saturated solution of methylene blue in methanol followed by a brief rinse with water.

Example 1: RVVPs expressing complement inhibitor activities are protected from inactivation by human serum.

LXSN RVVPs were prepared in the parent GPE86-LXSN3 producer cells described above. RVVPs were also prepared from clones of the CIM/gp70 transfected GPE86-LXSN producers cells described above that had been selected in hygromycin B. RVVPs from unmodified GPE86-LXSN3 producer cells, as well as from the cells transfected with the DAF/GP70, CCPH/GP70, and CD59/GP70 chimeric fusion expression vectors, were assayed in 40% human serum (in buffer) using the complement resistance titer assay as described above. As shown in FIG. 1, RVVPs produced by cells expressing the chimeric proteins encoded by each chimeric vector were substantially protected from complement inactivation as compared to RVVPs produced by unmodified GPE86-LXSN3 producer cells.

Example 2: RVVPs expressing a complement inhibitor activity are protected from inactivation by human whole blood.

Figure 2:
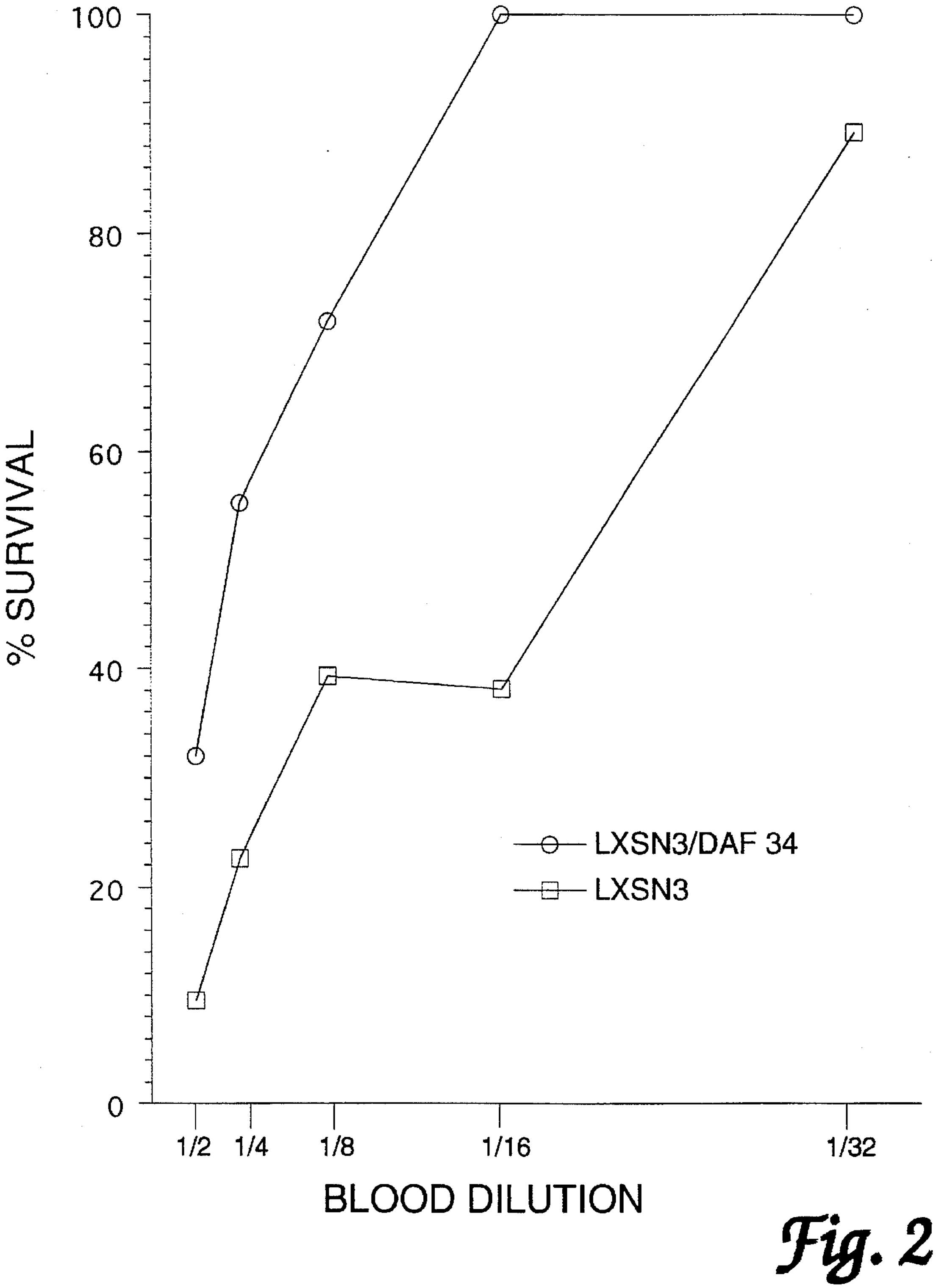

RVVPs prepared from the parent GPE86-LXSN3 producer cells described above and from LXSN3/DAF34 producer cells (expressing the chimeric DAF/gp70 protein encoded by plasmid DAF/gp70E described above) were assayed in whole human blood using the complement resistance titer assay as described above. As shown in FIG. 2, RVVPs produced by clone LXSN3/DAF34 were substantially protected from complement inactivation as compared to RVVPs produced by unmodified GPE86-LXSN3 producer cells.

DEPOSITS

Plasmids pKS-/mCCPH, CCPH/gp70E, pCDGPI#1-pCDNAI-Amp, CD59/gp70E and DAF/gp70E, discussed above, have been deposited with the American Type Culture Collection, 12301 Parklawn Drive, Rockville, Md., 20852, United States of America, in *E. coli* and have been assigned the designations 69178, 69650, 69564, 69652, and 69651 respectively. These deposits were made under the Budapest Treaty on the International Recognition of the Deposit of Micro-organisms for the Purposes of Patent Procedure (1977).

Throughout this application, various publications, patents, and patent applications have been referred to. The teachings and disclosures of these publications, patents, and patent applications in their entireties are hereby incorporated by reference into this application to more fully describe the state of the art to which the present invention pertains.

Although preferred and other embodiments of the invention have been described herein, other embodiments may be perceived by those skilled in the art without departing from the scope of the invention as defined by the following claims.

REFERENCES

Adams et al., 1991. *J Immunol* 147, pp. 3005–3011.

Albrecht and Fleckenstein, 1992. *J Virology* 66(6), pp. 3937–3940.

Albrecht et al., 1992. *Virology* 190, pp. 527–530.

Anderson, 1992. *Science* 256, pp. 808–813.

Ausubel et al., 1992. *Current Protocols in Molecular Biology*, Wiley Interscience, John Wiley and Sons, New York. Volume 1, Section III, units 9.10.1–9.14.3.

Bartholomew et al., 1978. *J Exp Med* 147, pp. 844–853.

Bartholomew et al., 1980. *Biochemistry* 19, pp. 2847–2853.

Bliska et al., 1992. *Proc Natl Acad Sci, USA* 89, pp. 3561–3565.

Boggs, 1990. *Int J Cell Cloning* 8, pp. 80–96.

Braga et al., 1992. *J Clin Invest* 90, pp. 1131–1137.

Chung et al., 1985. *Biochem* 256, pp. 133.

Cone and Mulligan, 1984. *Proc Natl Acad Sci, USA* 81, pp. 6349–6353.

Cooper et al., 1976. *J Exp Med* 144, pp. 970–984.

Cooper, 1991. *Immunol Today* 12, pp. 327–331.

Cosset et al., 1990. *J Virol* 64, pp. 1070–1078.

Coyne et al., 1992. *J Immunol* 149, pp. 2096.

Culver et al., 1992. *Science* 256, pp. 1550–1552.

Davies et al., 1989. *J Exp Med* 170, pp. 637–654.

Doolittle et al., 1979. *Quart Rev Biol* 64, pp. 1–29.

Eglitis et al., 1988. *Biotechniques* 6, pp. 608–614.

Eglitis, 1991. *Human Gene Therapy* 2, 195–201.

Eldering, 1992. *J Biol Chem* 263, pp. 11776–11779.

Felgner and Rhodes, 1991. *Nature* 349, pp. 351–352.

Fujita et al., 1987. *J Exp Med* 166, pp. 1221.

Galili et al., 1987. *Proc Natl Acad Sci, USA* 84, pp. 1369–1373.

Gilboa, 1986. *Biotechniques* 4, pp. 504–512.

Gooding, 1992. *Cell* 71, pp. 5–7.

Gumley et al., 1992. *J Immunol* 149, pp. 2615–2618.
Heffernan et al., 1992. *J Bacteriol* 174, pp. 84–91.
Hirt, 1967. *J Mol Biol* 26, 365–369.
Hong et al., 1990. *Infect and Immunol* 58, pp. 2535–2541.
Isaacs et al., 1992. *Proc Natl Acad Sci, USA* 89, pp. 628–632.
Kohn et al., 1989. *Cancer Invest* 7, pp. 179–192.
Korman et al., 1987. *Proc Natl Acad Sci, USA* 84, pp. 2150–2154.
Langer, 1990. *Science* 249, pp. 1527–1533.
Lehn, 1990. *Bone Marrow Transplantation* 5, pp. 287–293.
Leventhal et al., 1993. *Transplantation* 55, pp. 857–866.
Lublin et al., 1988. *J Exp Med* 168, pp. 181–194.
Lublin et al., 1989. *Ann Rev Immunol* 7, pp. 35–58.
Mann et al., 1983. *Cell* 33, pp. 153–159.
Markowitz et al., 1988. *J Virol* 62, pp. 1120–1124.
McNearney et al., 1987. *J Exp Med* 166, pp. 1525–1535.
Medof et al., 1984. *J Exp Med* 160, pp. 1558.
Miller and Buttimore, 1986. *Mol Cell Biol* 6, pp. 2895–2902.
Miller and Rosman, 1989. *Biotechniques* 7, pp. 980–990.
Miller et al., 1989. *Biotechniques* 7, pp. 981–990.
Miller, 1992. Nature 357, pp. 455–460.
Moran et al., 1992. *J Immunol* 140, pp. 1736–1743.
Morgenstern and Land, 1990. *Nucleic Acids Res* 18, pp. 3587–3596.
Muenchau et al., 1992. *Virology* 186, pp. 161–166.
Mulligan, 1983. *In Experimental Manipulation of Gene Expression* Inouye (ed), pp. 155–173.
Mulligan, 1993. *Science* 260, pp. 926–932.
Neethling et al., 1994. *Transplantation* 57, pp. 959–963.
Norris et al., 1991. *J Immunol* 147, pp. 2240–2247.
Okada et al., 1989. *J Immunol* 143, pp. 2262–2266.
Perkins et al., 1988. *Biochemistry* 27, pp. 4004.
Petranka et al., 1992. *Proc Natl Acad Sci, USA* 89, pp. 7876–7879.
Philbrick et al., 1990. *Eur J Immunol* 20, pp. 87–92.
Pramoonjago et al., 1992. *J Immunol* 148, pp. 827–836.
Ram et al., 1993. *J Neurosurg* 79, pp. 400–407.
*Remington's Pharmaceutical Sciences,* 1985. Mack Publishing Company, Philadelphia, Pa., 17th ed., chapters 37–39.
Ripoche et al., 1988. *Biochem J* 249, pp. 6122–6126.
Roitt et al., 1988. *Essential Immunology, 6th Ed.* Backwell Scientific Publications, Oxford, England.
Roldan et al., 1990. EMBO J 9, pp. 467–474.
Rollins et al., 1990. *J Immunol* 144, pp. 3478–3483.
Rother et al., 1994. *J Virology* 68(2), pp. 730–737.
Sambrook et al., 1989. *Molecular Cloning A Laboratory Manual, 2nd Ed.* Cold Spring Harbor Laboratory, Cold Spring Harbor, N.Y.
Sawada et al., 1989. *DNA Cell Biol* 9, pp. 213–220.
Shevach et al., 1989. *Immunol Today* 10, pp. 195–200.
Tone et al., 1992. *J Mol Biol* 227, pp. 971–976.
Tschopp et al., 1988. *Biochemistry* 27, pp. 4103–4109.
Varmus and Brown, 1989. *Retroviruses* in Berg and Howe (eds.), *Mobile DNA*, American Society for Microbiology, Washington, D.C.
Venneker et al., 1992. Exp Clin Immunogenet 9, pp. 33–47.
Verma, 1990. *Scientific American* 263(5), pp. 68–84.
Weatherall, 1991. *Nature* 349, pp. 275–276.
Weiss et al., (eds.), 1985. *RNA Tumor Viruses*, Cold Spring Harbor Laboratory, NY. Vol 1, pp. 31–34, 46–51, and Vol 2, pp. 2–7.
Welsh et al., 1975. *Nature* 257, pp. 612–614.
Welsh et al., 1976. *Virology* 74, pp. 432–440.
Widner and Brundin, 1988. *Brain Research Reviews* 13, pp. 287–324.
Williams et al., 1988. *Immunogenetics* 27, pp. 265–272.
Wong et al., 1985. *Proc Natl Acad Sci, USA.* 82, pp. 7711.
Yates et al., 1985. *Nature* 313, pp. 811–815.

What is claimed is:

1. A retroviral vector particle expressing a complement inhibitor activity, wherein the retroviral vector 9article is substantially protected from inactivation upon exposure to body fluids containing complement.

2. The retroviral vector particle of claim 1 wherein the complement inhibitor activity is a DAF activity.

3. The retroviral vector particle of claim 1 wherein the complement inhibitor activity is a CCPH activity.

4. The retroviral vector particle of claim 1 wherein the complement inhibitor activity is a CD59 activity.

5. A method for transducing a cell with a retroviral vector in the presence of a body fluid containing complement, wherein said method comprises administering the retrovital vector particle of claim 1 to the cell.

6. The method of claim 5, wherein the retroviral vector particle is administered to the cell ex vivo.

7. A retroviral producer cell producing the retrovital vector particles of claim 1.

8. A retroviral vector particle having a chimeric envelope protein, wherein the chimeric envelope protein is an envelope protein with at least a portion of the N-terminal receptor binding domain removed and replaced with a protein domain having a complement inhibitor activity.

9. The retroviral vector particle of claim 8 wherein the complement inhibitor activity is a DAF activity.

10. The retroviral vector particle of claim 8 wherein the complement inhibitor activity is a CCPH activity.

11. The retroviral vector particle of claim 8 wherein the complement inhibitor activity is a CD59 activity.

12. A retroviral producer cell producing the retroviral vector particles of claim 8.

13. A method for transducing a cell with a retroviral vector in the presence of a body fluid containing complement, wherein said method comprises administering the retroviral vector particle of claim 8 to the cell.

14. The method of claim 13, wherein the retroviral vector particle is administered to the cell ex vivo.

15. A method for transducing a cell ex vivo with a retroviral vector in the presence of a body fluid containing complement, wherein said method comprises administering the retroviral vector particle of claim 8 to the cell in culture.

16. A method for transducing a cell ex vivo with a retrovital vector in the presence of a body fluid containing complement, wherein said method comprises administering the retroviral vector particle of claim 1 to the cell in culture.

17. A chimeric retroviral envelope protein with at least a portion of the N-terminal receptor binding domain removed and replaced with a protein domain having a complement inhibitor activity.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 60 bases
( B ) TYPE: Nucleic Acid
( C ) STRANDEDNESS: Single
( D ) TOPOLOGY: Linear ( i i ) MOLECULE TYPE: Other nucleic acid
( A ) DESCRIPTION: 5'Flag-mCCPH 5'PCR primer ( i i i ) HYPOTHETICAL: No ( i v ) ANTI-SENSE: No ( x i ) SEQUENCE DESCRIPTION: SEQ ID NO:1:

GCCGGCCTGC AGGACTACAA AGACGATGAC GATAAATTAA GCTGTCCTAC 50

ACGTAACCAG 60

( 2 ) INFORMATION FOR SEQ ID NO:2:

( i ) SEQUENCE CHARACTERISTICS:
( A ) LENGTH: 23 bases
( B ) TYPE: Nucleic Acid

-continued ( C ) STRANDEDNESS: Single
( D ) TOPOLOGY: Linear ( i i ) MOLECULE TYPE: Other nucleic acid
( A ) DESCRIPTION: 5'Flag-mCCPH 3'PCR primer ( i i i ) HYPOTHETICAL: No ( i v ) ANTI-SENSE: Yes ( x i ) SEQUENCE DESCRIPTION: SEQ ID NO:2:

CTTCCATTTA AAAGATCTTG CGG 23

( 2 ) INFORMATION FOR SEQ ID NO:3:

( i ) SEQUENCE CHARACTERISTICS:
( A ) LENGTH: 239 base pairs
( B ) TYPE: Nucleic Acid
( C ) STRANDEDNESS: Double
( D ) TOPOLOGY: Linear ( i i ) MOLECULE TYPE: Other nucleic acid
( A ) DESCRIPTION: CCPH PCR product ( i i i ) HYPOTHETICAL: No ( i v ) ANTI-SENSE: No ( x i ) SEQUENCE DESCRIPTION: SEQ ID NO:3:

CTGCAGGACT ACAAAGACGA TGACGATAAA TTAAGCTGTC CTACACGTAA 50

CCAGTATGTT TCTGTCAAAT ATGTGAATCT AACTAACTAT TCAGGCCCGT 100

ATCCAAACGG GACAACGCTA CACGTGACAT GCCGTGAAGG ATATGCAAAA 150

AGACCAGTAC AAACTGTTAC ATGCGTCAAT GGTAACTGGA CTGTACCTAA 200

AAAGTGTCAG AAAAAGAAAT GTTCTACACC GCAAGATCT 239

( 2 ) INFORMATION FOR SEQ ID NO:4:

( i ) SEQUENCE CHARACTERISTICS:
( A ) LENGTH: 21 base pairs
( B ) TYPE: Nucleic Acid
( C ) STRANDEDNESS: Double
( D ) TOPOLOGY: Circular ( i i ) MOLECULE TYPE: Other nucleic acid
( A ) DESCRIPTION: CCPH/gp70E Junction ( i i i ) HYPOTHETICAL: No ( i v ) ANTI-SENSE: No ( x i ) SEQUENCE DESCRIPTION: SEQ ID NO:4:

TGT ATG AAG ATA GAC GGA GCC 21
Cys Met Lys Ile Asp Gly Ala
1 5

( 2 ) INFORMATION FOR SEQ ID NO:5:

( i ) SEQUENCE CHARACTERISTICS:
( A ) LENGTH: 21 base pairs
( B ) TYPE: Nucleic Acid
( C ) STRANDEDNESS: Double
( D ) TOPOLOGY: Circular ( i i ) MOLECULE TYPE: Other nucleic acid
( A ) DESCRIPTION: CD59/gp70E Junction ( i i i ) HYPOTHETICAL: No ( i v ) ANTI-SENSE: No ( x i ) SEQUENCE DESCRIPTION: SEQ ID NO:5:

```
GGT GGA GCG GCC GGA CAA GAT                                        21
Gly Gly Ala Ala Gly Gln Asp
1               5
```

( 2 ) INFORMATION FOR SEQ ID NO:6:

( i ) SEQUENCE CHARACTERISTICS:
( A ) LENGTH: 21 base pairs
( B ) TYPE: Nucleic Acid
( C ) STRANDEDNESS: Double
( D ) TOPOLOGY: Circular ( i i ) MOLECULE TYPE: Other nucleic acid
( A ) DESCRIPTION: DAF/gp70E Junction ( i i i ) HYPOTHETICAL: No ( i v ) ANTI-SENSE: No ( x i ) SEQUENCE DESCRIPTION: SEQ ID NO:6:

```
CCT GAA TGC AGT GGG ACT CCT                                        21
Pro Glu Cys Ser Gly Thr Pro
1               5
```

( 2 ) INFORMATION FOR SEQ ID NO:7:

( i ) SEQUENCE CHARACTERISTICS:
( A ) LENGTH: 1407 bases
( B ) TYPE: Nucleic acid
( C ) STRANDEDNESS: Single
( D ) TOPOLOGY: Linear ( i i ) MOLECULE TYPE: cDNA to genomic RNA
( A ) DESCRIPTION: Ecotropic gp70 protein ( i i i ) HYPOTHETICAL: No ( i v ) ANTI-SENSE: No ( x ) PUBLICATION INFORMATION:
( A ) AUTHORS: Shinnick, T. M.
Lerner, R. A.
Sutcliffe, J. G.
( B ) TITLE: Nucleotide sequence of
Moloney murine leukemia virus.
( C ) JOURNAL: Nature
( D ) VOLUME: 293
( F ) PAGES: 543-548
( G ) DATE: 1981

( x i ) SEQUENCE DESCRIPTION: SEQ ID NO:7:

```
ATG GCG CGT TCA ACG CTC TCA AAA CCC CTT AAA AAT AAG GTT             42
Met Ala Arg Ser Thr Leu Ser Lys Pro Leu Lys Asn Lys Val
  1             5                   10

AAC CCG CGA GGC CCC CTA ATC CCC TTA ATT CTT CTG ATG CTC             84
Asn Pro Arg Gly Pro Leu Ile Pro Leu Ile Leu Leu Met Leu
 15                 20                  25

AGA GGG GTC AGT ACT GCT TCG CCC GGC TCC AGT CCT CAT CAA            126
Arg Gly Val Ser Thr Ala Ser Pro Gly Ser Ser Pro His Gln
     30                 35                  40

GTC TAT AAT ATC ACC TGG GAG GTA ACC AAT GGA GAT CGG GAG            168
Val Tyr Asn Ile Thr Trp Glu Val Thr Asn Gly Asp Arg Glu
         45                 50                  55

ACG GTA TGG GCA ACT TCT GGC AAC CAC CCT CTG TGG ACC TGG            210
Thr Val Trp Ala Thr Ser Gly Asn His Pro Leu Trp Thr Trp
             60                 65                  70

TGG CCT GAC CTT ACC CCA GAT TTA TGT ATG TTA GCC CAC CAT            252
Trp Pro Asp Leu Thr Pro Asp Leu Cys Met Leu Ala His His
                 75                 80
```

-continued

```
GGA CCA TCT TAT TGG GGG CTA GAA TAT CAA TCC CCT TTT TCT   294
Gly Pro Ser Tyr Trp Gly Leu Glu Tyr Gln Ser Pro Phe Ser
 85                  90                  95

TCT CCC CCG GGG CCC CCT TGT TGC TCA GGG GGC AGC AGC CCA   336
Ser Pro Pro Gly Pro Pro Cys Cys Ser Gly Gly Ser Ser Pro
    100                 105                 110

GGC TGT TCC AGA GAC TGC GAA GAA CCT TTA ACC TCC CTC ACC   378
Gly Cys Ser Arg Asp Cys Glu Glu Pro Leu Thr Ser Leu Thr
        115                 120                 125

CCT CGG TGC AAC ACT GCC TGG AAC AGA CTC AAG CTA GAC CAG   420
Pro Arg Cys Asn Thr Ala Trp Asn Arg Leu Lys Leu Asp Gln
            130                 135                 140

ACA ACT CAT AAA TCA AAT GAG GGA TTT TAT GTT TGC CCC GGG   462
Thr Thr His Lys Ser Asn Glu Gly Phe Tyr Val Cys Pro Gly
                145                 150

CCC CAC CGC CCC CGA GAA TCC AAG TCA TGT GGG GGT CCA GAC   504
Pro His Arg Pro Arg Glu Ser Lys Ser Cys Gly Gly Pro Asp
155                 160                 165

TCC TTC TAC TGT GCC TAT TGG GGC TGT GAG ACA ACC GGT AGA   546
Ser Phe Tyr Cys Ala Tyr Trp Gly Cys Glu Thr Thr Gly Arg
    170                 175                 180

GCT TAC TGG AAG CCC TCC TCA TCA TGG GAT TTC ATC ACA GTA   588
Ala Tyr Trp Lys Pro Ser Ser Ser Trp Asp Phe Ile Thr Val
        185                 190                 195

AAC AAC AAT CTC ACC TCT GAC CAG GCT GTC CAG GTA TGC AAA   630
Asn Asn Asn Leu Thr Ser Asp Gln Ala Val Gln Val Cys Lys
            200                 205                 210

GAT AAT AAG TGG TGC AAC CCC TTA GTT ATT CGG TTT ACA GAC   672
Asp Asn Lys Trp Cys Asn Pro Leu Val Ile Arg Phe Thr Asp
                215                 220

GCC GGG AGA CGG GTT ACT TCC TGG ACC ACA GGA CAT TAC TGG   714
Ala Gly Arg Arg Val Thr Ser Trp Thr Thr Gly His Tyr Trp
225                 230                 235

GGC TTA CGT TTG TAT GTC TCC GGA CAA GAT CCA GGG CTT ACA   756
Gly Leu Arg Leu Tyr Val Ser Gly Gln Asp Pro Gly Leu Thr
    240                 245                 250

TTT GGG ATC CGA CTC AGA TAC CAA AAT CTA GGA CCC CGC GTC   798
Phe Gly Ile Arg Leu Arg Tyr Gln Asn Leu Gly Pro Arg Val
        255                 260                 265

CCA ATA GGG CCA AAC CCC GTT CTG GCA GAC CAA CAG CCA CTC   840
Pro Ile Gly Pro Asn Pro Val Leu Ala Asp Gln Gln Pro Leu
            270                 275                 280

TCC AAG CCC AAA CCT GTT AAG TCG CCT TCA GTC ACC AAA CCA   882
Ser Lys Pro Lys Pro Val Lys Ser Pro Ser Val Thr Lys Pro
                285                 290

CCC AGT GGG ACT CCT CTC TCC CCT ACC CAA CTT CCA CCG GCG   924
Pro Ser Gly Thr Pro Leu Ser Pro Thr Gln Leu Pro Pro Ala
295                 300                 305

GGA ACG GAA AAT AGG CTG CTA AAC TTA GTA GAC GGA GCC TAC   966
Gly Thr Glu Asn Arg Leu Leu Asn Leu Val Asp Gly Ala Tyr
    310                 315                 320

CAA GCC CTC AAC CTC ACC AGT CCT GAC AAA ACC CAA GAG TGC  1008
Gln Ala Leu Asn Leu Thr Ser Pro Asp Lys Thr Gln Glu Cys
        325                 330                 335

TGG TTG TGT CTA GTA GCG GGA CCC CCC TAC TAC GAA GGG GTT  1050
Trp Leu Cys Leu Val Ala Gly Pro Pro Tyr Tyr Glu Gly Val
            340                 345                 350

GCC GTC CTG GGT ACC TAC TCC AAC CAT ACC TCT GCT CCA GCC  1092
Ala Val Leu Gly Thr Tyr Ser Asn His Thr Ser Ala Pro Ala
                355                 360
```

-continued

AAC TGC TCC GTG GCC TCC CAA CAC AAG TTG ACC CTG TCC GAA 1134
Asn Cys Ser Val Ala Ser Gln His Lys Leu Thr Leu Ser Glu
365 370 375

GTG ACC GGA CAG GGA CTC TGC ATA GGA GCA GTT CCC AAA ACA 1176
Val Thr Gly Gln Gly Leu Cys Ile Gly Ala Val Pro Lys Thr
380 385 390

CAT CAG GCC CTA TGT AAT ACC ACC CAG ACA AGC AGT CGA GGG 1218
His Gln Ala Leu Cys Asn Thr Thr Gln Thr Ser Ser Arg Gly
395 400 405

TCC TAT TAT CTA GTT GCC CCT ACA GGT ACC ATG TGG GCT TGT 1260
Ser Tyr Tyr Leu Val Ala Pro Thr Gly Thr Met Trp Ala Cys
410 415 420

AGT ACC GGG CTT ACT CCA TGC ATC TCC ACC ACC ATA CTG AAC 1302
Ser Thr Gly Leu Thr Pro Cys Ile Ser Thr Thr Ile Leu Asn
425 430

CTT ACC ACT GAT TAT TGT GTT CTT GTC GAA CTC TGG CCA AGA 1344
Leu Thr Thr Asp Tyr Cys Val Leu Val Glu Leu Trp Pro Arg
435 440 445

GTC ACC TAT CAT TCC CCC AGC TAT GTT TAC GGC CTG TTT GAG 1386
Val Thr Tyr His Ser Pro Ser Tyr Val Tyr Gly Leu Phe Glu
450 455 460

AGA TCC AAC CGA CAC AAA AGA 1407
Arg Ser Asn Arg His Lys Arg
465

( 2 ) INFORMATION FOR SEQ ID NO:8:

( i ) SEQUENCE CHARACTERISTICS:
( A ) LENGTH: 1329 bases
( B ) TYPE: Nucleic acid
( C ) STRANDEDNESS: Single
( D ) TOPOLOGY: Linear ( i i ) MOLECULE TYPE: cDNA to genomic RNA
( A ) DESCRIPTION: Xenotropic gp70 protein ( i i i ) HYPOTHETICAL: No ( i v ) ANTI-SENSE: No ( x ) PUBLICATION INFORMATION:
( A ) AUTHORS: Massey, A. C.
Coppola, M. A.
Thomas, C. Y.
( B ) TITLE: Origin of pathogenic determinants of recombinant murine leukemia viruses: Analysis of Bxv-1-related xenotropic viruses from CWD mice.
( C ) JOURNAL: Journal of Virology
( D ) VOLUME: 64
( F ) PAGES: 5491-5499
( G ) DATE: 1990

( x i ) SEQUENCE DESCRIPTION: SEQ ID NO:8:

ATG GAA GGT CCA GCG TTC TCA AAA CCC CTT AAA GAT AAG ATT 42
Met Glu Gly Pro Ala Phe Ser Lys Pro Leu Lys Asp Lys Ile
1 5 10

AAC CCG TGG GGC CCC CTA ATA GTT ATA GGG ATC TTG GTG AGG 84
Asn Pro Trp Gly Pro Leu Ile Val Ile Gly Ile Leu Val Arg
15 20 25

GCA GGA GCC TCG GTA CAA CGT GAC AGC CCT CAC CAG GTC TTC 126
Ala Gly Ala Ser Val Gln Arg Asp Ser Pro His Gln Val Phe
30 35 40

AAT GTC ACT TGG AGA GTT ACC AAC CTA ATG ACA GGA CAA ACA 168
Asn Val Thr Trp Arg Val Thr Asn Leu Met Thr Gly Gln Thr
45 50 55

-continued

```
GCT AAC GCT ACC TCC CTC CTG GGG ACG ATG ACA GAC ACC TTC     210
Ala Asn Ala Thr Ser Leu Leu Gly Thr Met Thr Asp Thr Phe
            60                  65                  70

CCT AAA CTA TAT TTT GAC TTG TGT GAT TTA GTT GGA GAC CAT     252
Pro Lys Leu Tyr Phe Asp Leu Cys Asp Leu Val Gly Asp His
                75                  80

TGG GAT GAC CCA GAA CCC GAT ATT GGA GAT GGT TGC CGC TCT     294
Trp Asp Asp Pro Glu Pro Asp Ile Gly Asp Gly Cys Arg Ser
85                  90                  95

CCC GGG GGA AGA AAA AGA TCA AGA CTG TAT GAC TTC TAT GTT     336
Pro Gly Gly Arg Lys Arg Ser Arg Leu Tyr Asp Phe Tyr Val
    100                 105                 110

TGC CCC GGT CAT ACT GTA CCA ATA GGG TGT GGA GGG CCG GGA     378
Cys Pro Gly His Thr Val Pro Ile Gly Cys Gly Gly Pro Gly
        115                 120                 125

GAG GGC TAC TGT GGC AAA TGG GGA TGT GAG ACC ACT GGA CAG     420
Glu Gly Tyr Cys Gly Lys Trp Gly Cys Glu Thr Thr Gly Gln
            130                 135                 140

GCA TAC TGG AAG CCA TCA TCA TCA TGG GAC CTA ATT TCC CTT     462
Ala Tyr Trp Lys Pro Ser Ser Ser Trp Asp Leu Ile Ser Leu
                145                 150

AAG CGA GGA AAC ACT CCT AAG GAT CAG GGC CCC TGT TAT GAT     504
Lys Arg Gly Asn Thr Pro Lys Asp Gln Gly Pro Cys Tyr Asp
155                 160                 165

TCC TCG GTC TCC AGT GGC GTC CAG GGT GCC ACA CCG GGG GGT     546
Ser Ser Val Ser Ser Gly Val Gln Gly Ala Thr Pro Gly Gly
    170                 175                 180

CGA TGC AAC CCC CTA GTC TTA GAA TTC ACT GAC GCG GGT AAA     588
Arg Cys Asn Pro Leu Val Leu Glu Phe Thr Asp Ala Gly Lys
        185                 190                 195

AAG GCC AGC TGG GAT GCC CCC AAA GTT TGG GGA CTA AGA CTC     630
Lys Ala Ser Trp Asp Ala Pro Lys Val Trp Gly Leu Arg Leu
            200                 205                 210

TAC CGA TCC ACA GGG GCC GAC CCG GTG ACC CGG TTC TCT TTG     672
Tyr Arg Ser Thr Gly Ala Asp Pro Val Thr Arg Phe Ser Leu
                215                 220

ACC CGC CAG GTC CTC AAT GTA GGA CCC CGC GTC CCC ATT GGG     714
Thr Arg Gln Val Leu Asn Val Gly Pro Arg Val Pro Ile Gly
225                 230                 235

CCT AAT CCC GTG ATC ACA GAA CAG CTA CCC CCC TCC CAA CCC     756
Pro Asn Pro Val Ile Thr Glu Gln Leu Pro Pro Ser Gln Pro
    240                 245                 250

GTG CAG ATC ATG CTC CCC AGG CCT CCT CAT CCT CCT CCT TCA     798
Val Gln Ile Met Leu Pro Arg Pro Pro His Pro Pro Pro Ser
        255                 260                 265

GGC GCG GCC TCT ATG GTC CCT GGG GCT CCC CCG CCT TCT CAA     840
Gly Ala Ala Ser Met Val Pro Gly Ala Pro Pro Pro Ser Gln
            270                 275                 280

CAA CCT GGG ACG GGG GAC AGG CTG CTA AAC CTA GTA AAA GGA     882
Gln Pro Gly Thr Gly Asp Arg Leu Leu Asn Leu Val Lys Gly
                285                 290

GCC TAT CAA GCA CTC AAC CTC ACC AGT CCT GAC AGA ACC CAA     924
Ala Tyr Gln Ala Leu Asn Leu Thr Ser Pro Asp Arg Thr Gln
295                 300                 305

GAG TGC TGG TTG TGT CTG GTA TCG GGA CCC CCC TAC TAC GAA     966
Glu Cys Trp Leu Cys Leu Val Ser Gly Pro Pro Tyr Tyr Glu
    310                 315                 320

GGG GTT GCC GTC CTA GGT ACC TAT TCC AAC CAT ACC TCT GCC    1008
Gly Val Ala Val Leu Gly Thr Tyr Ser Asn His Thr Ser Ala
        325                 330                 335
```

-continued

CCA GCT AAC TGC TCC GTG GCC TCC CAA CAC AAG CTG ACC CTG 1050
Pro Ala Asn Cys Ser Val Ala Ser Gln His Lys Leu Thr Leu
340 345 350

TCC GAA GTG ACC GGG CAG GGA CTC TGC GTA GGA GCA GTT CCC 1092
Ser Glu Val Thr Gly Gln Gly Leu Cys Val Gly Ala Val Pro
355 360

AAA ACC CAT CAG GCC CTG TGT AAT ACC ACC CAG AAG GCG AGC 1134
Lys Thr His Gln Ala Leu Cys Asn Thr Thr Gln Lys Ala Ser
365 370 375

GAC GGG TCC TAC TAT CTG GCT GCT CCC GCC GGG ACC ATC TGG 1176
Asp Gly Ser Tyr Tyr Leu Ala Ala Pro Ala Gly Thr Ile Trp
380 385 390

GCT TGC AAC ACC GGG CTC ACT CCC TGC CTA TCT ACC ACT GTA 1218
Ala Cys Asn Thr Gly Leu Thr Pro Cys Leu Ser Thr Thr Val
395 400 405

CTC AAC CTC ACC ACC GAT TAC TGT GTC CTG GTT GAG CTC TGG 1260
Leu Asn Leu Thr Thr Asp Tyr Cys Val Leu Val Glu Leu Trp
410 415 420

CCA AAG GTG ACC TAC CAC TCC CCT GGT TAT GTT TAT GAC CAG 1302
Pro Lys Val Thr Tyr His Ser Pro Gly Tyr Val Tyr Asp Gln
425 430

TTT GAG AGA AAA ACC AAA TAT AAA AGA 1329
Phe Glu Arg Lys Thr Lys Tyr Lys Arg
435 440

( 2 ) INFORMATION FOR SEQ ID NO:9:

( i ) SEQUENCE CHARACTERISTICS:
( A ) LENGTH: 1374 bases
( B ) TYPE: Nucleic acid
( C ) STRANDEDNESS: Single
( D ) TOPOLOGY: Linear ( i i ) MOLECULE TYPE: cDNA to genomic RNA
( A ) DESCRIPTION: Amphotropic gp70 protein ( i i i ) HYPOTHETICAL: No ( i v ) ANTI-SENSE: No ( x ) PUBLICATION INFORMATION:
( A ) AUTHORS: Ott, D.
Friedrich, R.
Rein, A.
( B ) TITLE: Sequence analysis of amphotropic and 10A1 murine leukemia viruses: Close relationship to mink cell focus-inducing viruses.
( C ) JOURNAL: Journal of Virology
( D ) VOLUME: 64
( F ) PAGES: 757-766
( G ) DATE: 1990

( x i ) SEQUENCE DESCRIPTION: SEQ ID NO:9:

ATG GCG 6
Met Ala
1

CGT TCA ACG CTC TCA AAA CCC CCT CAA GAT AAG ATT AAC CCG 48
Arg Ser Thr Leu Ser Lys Pro Pro Gln Asp Lys Ile Asn Pro
5 10 15

TGG AAG CCC TTA ATA GTC ATG GGA GTC CTG TTA GGA GTA GGG 90
Trp Lys Pro Leu Ile Val Met Gly Val Leu Leu Gly Val Gly
20 25 30

ATG GCA GAG AGC CCC CAT CAG GTC TTT AAT GTA ACC TGG AGA 132
Met Ala Glu Ser Pro His Gln Val Phe Asn Val Thr Trp Arg
35 40

-continued

```
GTC ACC AAC CTG ATG ACT GGG CGT ACC GCC AAT GCC ACC TCC     174
Val Thr Asn Leu Met Thr Gly Arg Thr Ala Asn Ala Thr Ser
 45                 50                  55

CTC CTG GGA ACT GTA CAA GAT GCC TTC CCA AAA TTA TAT TTT     216
Leu Leu Gly Thr Val Gln Asp Ala Phe Pro Lys Leu Tyr Phe
     60                 65                  70

GAT CTA TGT GAT CTG GTC GGA GAG GAG TGG GAC CCT TCA GAC     258
Asp Leu Cys Asp Leu Val Gly Glu Glu Trp Asp Pro Ser Asp
         75                 80                  85

CAG GAA CCG TAT GTC GGG TAT GGC TGC AAG TAC CCC GCA GGG     300
Gln Glu Pro Tyr Val Gly Tyr Gly Cys Lys Tyr Pro Ala Gly
             90                 95                  100

AGA CAG CGG ACC CGG ACT TTT GAC TTT TAC GTG TGC CCT GGG     342
Arg Gln Arg Thr Arg Thr Phe Asp Phe Tyr Val Cys Pro Gly
                105                 110

CAT ACC GTA AAG TCG GGG TGT GGG GGA CCA GGA GAG GGC TAC     384
His Thr Val Lys Ser Gly Cys Gly Gly Pro Gly Glu Gly Tyr
115                 120                 125

TGT GGT AAA TGG GGG TGT GAA ACC ACC GGA CAG GCT TAC TGG     426
Cys Gly Lys Trp Gly Cys Glu Thr Thr Gly Gln Ala Tyr Trp
    130                 135                 140

AAG CCC ACA TCA TCG TGG GAC CTA ATC TCC CTT AAG CGC GGT     468
Lys Pro Thr Ser Ser Trp Asp Leu Ile Ser Leu Lys Arg Gly
        145                 150                 155

AAC ACC CCC TGG GAC ACG GGA TGC TCT AAA GTT GCC TGT GGC     510
Asn Thr Pro Trp Asp Thr Gly Cys Ser Lys Val Ala Cys Gly
            160                 165                 170

CCC TGC TAC GAC CTC TCC AAA GTA TCC AAT TCC TTC CAA GGG     552
Pro Cys Tyr Asp Leu Ser Lys Val Ser Asn Ser Phe Gln Gly
                175                 180

GCT ACT CGA GGG GGC AGA TGC AAC CCT CTA GTC CTA GAA TTC     594
Ala Thr Arg Gly Gly Arg Cys Asn Pro Leu Val Leu Glu Phe
185                 190                 195

ACT GAT GCA GGA AAA AAG GCT AAC TGG GAC GGG CCC AAA TCG     636
Thr Asp Ala Gly Lys Lys Ala Asn Trp Asp Gly Pro Lys Ser
    200                 205                 210

TGG GGA CTG AGA CTG TAC CGG ACA GGA ACA GAT CCT ATT ACC     678
Trp Gly Leu Arg Leu Tyr Arg Thr Gly Thr Asp Pro Ile Thr
        215                 220                 225

ATG TTC TCC CTG ACC CGG CAG GTC CTT AAT GTG GGA CCC CGA     720
Met Phe Ser Leu Thr Arg Gln Val Leu Asn Val Gly Pro Arg
            230                 235                 240

GTC CCC ATA GGG CCC AAC CCA GTA TTA CCC GAC CAA AGA CTC     762
Val Pro Ile Gly Pro Asn Pro Val Leu Pro Asp Gln Arg Leu
                245                 250

CCT TCC TCA CCA ATA GAG ATT GTA CCG GCT CCA CAG CCA CCT     804
Pro Ser Ser Pro Ile Glu Ile Val Pro Ala Pro Gln Pro Pro
255                 260                 265

AGC CCC CTC AAT ACC AGT TAC CCC CCT TCC ACT ACC AGT ACA     846
Ser Pro Leu Asn Thr Ser Tyr Pro Pro Ser Thr Thr Ser Thr
    270                 275                 280

CCC TCA ACC TCC CCT ACA AGT CCA AGT GTC CCA CAG CCA CCC     888
Pro Ser Thr Ser Pro Thr Ser Pro Ser Val Pro Gln Pro Pro
        285                 290                 295

CCA GGA ACT GGA GAT AGA CTA CTA GCT CTA GTC AAA GGA GCC     930
Pro Gly Thr Gly Asp Arg Leu Leu Ala Leu Val Lys Gly Ala
            300                 305                 310

TAT CAG GCG CTT AAC CTC ACC AAT CCC GAC AAG ACC CAA GAA     972
Tyr Gln Ala Leu Asn Leu Thr Asn Pro Asp Lys Thr Gln Glu
                315                 320
```

-continued

```
TGT TGG CTG TGC TTA GTG TCG GGA CCT CCT TAT TAC GAA GGA     1014
Cys Trp Leu Cys Leu Val Ser Gly Pro Pro Tyr Tyr Glu Gly
325                 330                 335

GTA GCG GTC GTG GGC ACT TAT ACC AAT CAT TCC ACC GCT CCG     1056
Val Ala Val Val Gly Thr Tyr Thr Asn His Ser Thr Ala Pro
    340                 345                 350

GCC AAC TGT ACG GCC ACT TCC CAA CAT AAG CTT ACC CTA TCT     1098
Ala Asn Cys Thr Ala Thr Ser Gln His Lys Leu Thr Leu Ser
        355                 360                 365

GAA GTG ACA GGA CAG GGC CTA TGC ATG GGG GCA GTA CCT AAA     1140
Glu Val Thr Gly Gln Gly Leu Cys Met Gly Ala Val Pro Lys
            370                 375                 380

ACT CAC CAG GCC TTA TGT AAC ACC ACC CAA AGC GCC GGC TCA     1182
Thr His Gln Ala Leu Cys Asn Thr Thr Gln Ser Ala Gly Ser
                385                 390

GGA TCC TAC TAC CTT GCA GCA CCC GCC GGA ACA ATG TGG GCT     1224
Gly Ser Tyr Tyr Leu Ala Ala Pro Ala Gly Thr Met Trp Ala
395                 400                 405

TGC AGC ACT GGA TTG ACT CCC TGC TTG TCC ACC ACG GTG CTC     1266
Cys Ser Thr Gly Leu Thr Pro Cys Leu Ser Thr Thr Val Leu
    410                 415                 420

AAT CTA ACC ACA GAT TAT TGT GTA TTA GTT GAA CTC TGG CCC     1308
Asn Leu Thr Thr Asp Tyr Cys Val Leu Val Glu Leu Trp Pro
        425                 430                 435

AGA GTA ATT TAC CAC TCC CCC GAT TAT ATG TAT GGT CAG CTT     1350
Arg Val Ile Tyr His Ser Pro Asp Tyr Met Tyr Gly Gln Leu
            440                 445                 450

GAA CAG CGT ACC AAA TAT AAA AGA                             1374
Glu Gln Arg Thr Lys Tyr Lys Arg
                455
```

( 2 ) INFORMATION FOR SEQ ID NO:10:

( i ) SEQUENCE CHARACTERISTICS:
( A ) LENGTH: 2096
( B ) TYPE: Nucleic Acid
( C ) STRANDEDNESS: Double
( D ) TOPOLOGY: Linear ( i i ) MOLECULE TYPE: cDNA to mRNA ( i i i ) HYPOTHETICAL: No ( i v ) ANTI-SENSE: No ( v i ) ORIGINAL SOURCE:
( A ) ORGANISM: Homo sapiens ( x ) PUBLICATION INFORMATION:
( A ) AUTHORS: Lublin, Douglas M.
Atkinson, John P.
( B ) TITLE: Decay-Accelerating Factor: Biochemistry, Molecular Biology, and Function
( C ) JOURNAL: Annual Review of Immunology
( D ) VOLUME: 7
( F ) PAGES: 35-58
( G ) DATE: 1989

( x i ) SEQUENCE DESCRIPTION: SEQ ID NO:10:

```
GCTGCGACTC GGCGGAGTCC CGGCGGCGCG TCCTTGTTCT                   40

AACCCGGCGC GCC ATG ACC GTC GCG CGG CCG AGC GTG CCC            80
               Met Thr Val Ala Arg Pro Ser Val Pro
                               -30

GCG GCG CTG CCC CTC CTC GGG GAG CTG CCC CGG CTG CTG CTG      122
Ala Ala Leu Pro Leu Leu Gly Glu Leu Pro Arg Leu Leu Leu
```

-continued

```
-25                 -20                 -15

CTG GTG CTG TTG TGC CTG CCG GCC GTG TGG GGT GAC TGT GGC     164
Leu Val Leu Leu Cys Leu Pro Ala Val Trp Gly Asp Cys Gly
    -10                 -5                  1

CTT CCC CCA GAT GTA CCT AAT GCC CAG CCA GCT TTG GAA GGC     206
Leu Pro Pro Asp Val Pro Asn Ala Gln Pro Ala Leu Glu Gly
     5                  10                  15

CGT ACA AGT TTT CCC GAG GAT ACT GTA ATA ACG TAC AAA TGT     248
Arg Thr Ser Phe Pro Glu Asp Thr Val Ile Thr Tyr Lys Cys
        20                  25                  30

GAA GAA AGC TTT GTG AAA ATT CCT GGC GAG AAG GAC TCA GTG     290
Glu Glu Ser Phe Val Lys Ile Pro Gly Glu Lys Asp Ser Val
            35                  40                  45

ACC TGC CTT AAG GGC ATG CAA TGG TCA GAT ATT GAA GAG TTC     332
Thr Cys Leu Lys Gly Met Gln Trp Ser Asp Ile Glu Glu Phe
                50                  55

TGC AAT CGT AGC TGC GAG GTG CCA ACA AGG CTA AAT TCT GCA     374
Cys Asn Arg Ser Cys Glu Val Pro Thr Arg Leu Asn Ser Ala
 60                 65                  70

TCC CTC AAA CAG CCT TAT ATC ACT CAG AAT TAT TTT CCA GTC     416
Ser Leu Lys Gln Pro Tyr Ile Thr Gln Asn Tyr Phe Pro Val
    75                  80                  85

GGT ACT GTT GTG GAA TAT GAG TGC CGT CCA GGT TAC AGA AGA     458
Gly Thr Val Val Glu Tyr Glu Cys Arg Pro Gly Tyr Arg Arg
        90                  95                  100

GAA CCT TCT CTA TCA CCA AAA CTA ACT TGC CTT CAG AAT TTA     500
Glu Pro Ser Leu Ser Pro Lys Leu Thr Cys Leu Gln Asn Leu
            105                 110                 115

AAA TGG TCC ACA GCA GTC GAA TTT TGT AAA AAG AAA TCA TGC     542
Lys Trp Ser Thr Ala Val Glu Phe Cys Lys Lys Lys Ser Cys
                120                 125

CCT AAT CCG GGA GAA ATA CGA AAT GGT CAG ATT GAT GTA CCA     584
Pro Asn Pro Gly Glu Ile Arg Asn Gly Gln Ile Asp Val Pro
130                 135                 140

GGT GGC ATA TTA TTT GGT GCA ACC ATC TCC TTC TCA TGT AAC     626
Gly Gly Ile Leu Phe Gly Ala Thr Ile Ser Phe Ser Cys Asn
    145                 150                 155

ACA GGG TAC AAA TTA TTT GGC TCG ACT TCT AGT TTT TGT CTT     668
Thr Gly Tyr Lys Leu Phe Gly Ser Thr Ser Ser Phe Cys Leu
        160                 165                 170

ATT TCA GGC AGC TCT GTC CAG TGG AGT GAC CCG TTG CCA GAG     710
Ile Ser Gly Ser Ser Val Gln Trp Ser Asp Pro Leu Pro Glu
            175                 180                 185

TGC AGA GAA ATT TAT TGT CCA GCA CCA CCA CAA ATT GAC AAT     752
Cys Arg Glu Ile Tyr Cys Pro Ala Pro Pro Gln Ile Asp Asn
                190                 195

GGA ATA ATT CAA GGG GAA CGT GAC CAT TAT GGA TAT AGA CAG     794
Gly Ile Ile Gln Gly Glu Arg Asp His Tyr Gly Tyr Arg Gln
200                 205                 210

TCT GTA ACG TAT GCA TGT AAT AAA GGA TTC ACC ATG ATT GGA     836
Ser Val Thr Tyr Ala Cys Asn Lys Gly Phe Thr Met Ile Gly
    215                 220                 225

GAG CAC TCT ATT TAT TGT ACT GTG AAT AAT GAT GAA GGA GAG     878
Glu His Ser Ile Tyr Cys Thr Val Asn Asn Asp Glu Gly Glu
        230                 235                 240

TGG AGT GGC CCA CCA CCT GAA TGC AGA GGA AAA TCT CTA ACT     920
Trp Ser Gly Pro Pro Pro Glu Cys Arg Gly Lys Ser Leu Thr
            245                 250                 255

TCC AAG GTC CCA CCA ACA GTT CAG AAA CCT ACC ACA GTA AAT     962
Ser Lys Val Pro Pro Thr Val Gln Lys Pro Thr Thr Val Asn
```

-continued

```
                260                                265

GTT  CCA  ACT  ACA  GAA  GTC  TCA  CCA  ACT  TCT  CAG  AAA  ACC  ACC           1004
Val  Pro  Thr  Thr  Glu  Val  Ser  Pro  Thr  Ser  Gln  Lys  Thr  Thr
270                      275                      280

ACA  AAA  ACC  ACC  ACA  CCA  AAT  GCT  CAA  GCA  ACA  CGG  AGT  ACA           1046
Thr  Lys  Thr  Thr  Thr  Pro  Asn  Ala  Gln  Ala  Thr  Arg  Ser  Thr
     285                      290                      295

CCT  GTT  TCC  AGG  ACA  ACC  AAG  CAT  TTT  CAT  GAA  ACA  ACC  CCA           1088
Pro  Val  Ser  Arg  Thr  Thr  Lys  His  Phe  His  Glu  Thr  Thr  Pro
          300                      305                      310

AAT  AAA  GGA  AGT  GGA  ACC  ACT  TCA  GGT  ACT  ACC  CGT  CTT  CTA           1130
Asn  Lys  Gly  Ser  Gly  Thr  Thr  Ser  Gly  Thr  Thr  Arg  Leu  Leu
               315                      320                      325

TCT  GGG  CAC  ACG  TGT  TTC  ACG  TTG  ACA  GGT  TTG  CTT  GGG  ACG           1172
Ser  Gly  His  Thr  Cys  Phe  Thr  Leu  Thr  Gly  Leu  Leu  Gly  Thr
                    330                      335

CTA  GTA  ACC  ATG  GGC  TTG  CTG  ACT                                         1196
Leu  Val  Thr  Met  Gly  Leu  Leu  Thr
340                      345

TAGCCAAAGA  AGAGTTAAGA  AGAAAATACA  CACAAGTATA  CAGACTGTTC                     1246

CTAGTTTCTT  AGACTTATCT  GCATATTGGA  TAAAATAAAT  GCAATTGTGC                     1296

TCTTCATTTA  GGATGCTTTC  ATTGTCTTTA  AGATGTGTTA  GGAATGTCAA                     1346

CAGAGCAAGG  AGAAAAAAGG  CAGTCCTGGA  ATCACATTCT  TAGCACACCT                     1396

GCGCCTCTTG  AAAATAGAAC  AACTTGCAGA  ATTGAGAGTG  ATTCCTTTCC                     1446

TAAAAGTGTA  AGAAAGCATA  GAGATTTGTT  CGTATTAAGA  ATGGGATCAC                     1496

GAGGAAAAGA  GAAGGAAAGT  GATTTTTTTC  CACAAGATCT  GAAATGATAT                     1546

TTCCACTTAT  AAAGGAAATA  AAAAATGAAA  AACATTATTT  GGATATCAAA                     1596

AGCAAATAAA  AACCCAATTC  AGTCTCTTCT  AAGCAAAATT  GCTAAAGAGA                     1646

GATGACCACA  TTATAAAGTA  ATCTTTGGCT  AAGGCATTTT  CATCTTTCCT                     1696

TCGGTTGGCA  AAATATTTTA  AAGGTAAAAC  ATGCTGGTGA  ACCAGGGTGT                     1746

TGATGGTGAT  AAGGGAGGAA  TATAGAATGA  AAGACTGAAT  CTTCCTTTGT                     1796

TGCACAAATA  GAGTTTGGAA  AAAGCCTGTG  AAAGGTGTCT  TCTTTGACTT                     1846

AATGTCTTTA  AAAGTATCCA  GAGATACTAC  AATATTAACA  TAAGAAAAGA                     1896

TTATATATTA  TTTCTGAATC  GAGATGTCCA  TAGTCAAATT  TGTAAATCTT                     1946

ATTCTTTTGT  AATATTTATT  TATATTTATT  TATGACAGTG  AACATTCTGA                     1996

TTTTACATGT  AAAACAAGAA  AAGTTGAAGA  AGATATGTGA  AGAAAAATGT                     2046

ATTTTTCCTA  AATAGAAATA  AATGATCCCA  TTTTTTGGTA  AAAAAAAAAA                     2096
```

( 2 ) INFORMATION FOR SEQ ID NO:11:

( i ) SEQUENCE CHARACTERISTICS:
( A ) LENGTH: 1139 bases
( B ) TYPE: Nucleic Acid
( C ) STRANDEDNESS: Double
( D ) TOPOLOGY: Linear ( i i ) MOLECULE TYPE: cDNA to mRNA
( A ) DESCRIPTION: CD59 full length cDNA ( i i i ) HYPOTHETICAL: No ( i v ) ANTI-SENSE: No ( v i ) ORIGINAL SOURCE:
( A ) ORGANISM: Homo sapiens -continued ( x ) PUBLICATION INFORMATION:
( A ) AUTHORS: Philbrick, W.M.
Palfree, R.G.E
Maher, S.E.
Bridgett, M.M.
Sirlin S.
Bothwell, A.L.M.
( B ) TITLE: The CD59 antigen is a structural homologue of murine Ly-6 antigens but lacks interferon inducibility.
( C ) JOURNAL: European Journal of Immunology
( D ) VOLUME: 20
( F ) PAGES: 87-92
( G ) DATE: JAN-1990

( x i ) SEQUENCE DESCRIPTION: SEQ ID NO:11:

```
CGCAGAAGCG GCTCGAGGCT GGAAGAGGAT CCTGGGCGCC GCAGGTTCTG          50

TGGACAATCA CA ATG GGA ATC CAA GGA GGG TCT GTC CTG TTC           92
              Met Gly Ile Gln Gly Gly Ser Val Leu Phe
              -25                 -20

GGG CTG CTG CTC GTC CTG GCT GTC TTC TGC CAT TCA GGT CAT        134
Gly Leu Leu Leu Val Leu Ala Val Phe Cys His Ser Gly His
-15                 -10                 -5

AGC CTG CAG TGC TAC AAC TGT CCT AAC CCA ACT GCT GAC TGC        176
Ser Leu Gln Cys Tyr Asn Cys Pro Asn Pro Thr Ala Asp Cys
    +1              5                   10

AAA ACA GCC GTC AAT TGT TCA TCT GAT TTT GAT GCG TGT CTC        218
Lys Thr Ala Val Asn Cys Ser Ser Asp Phe Asp Ala Cys Leu
    15                  20                  25

ATT ACC AAA GCT GGG TTA CAA GTG TAT AAC AAG TGT TGG AAG        260
Ile Thr Lys Ala Gly Leu Gln Val Tyr Asn Lys Cys Trp Lys
        30                  35                  40

TTT GAG CAT TGC AAT TTC AAC GAC GTC ACA ACC CGC TTG AGG        302
Phe Glu His Cys Asn Phe Asn Asp Val Thr Thr Arg Leu Arg
            45                  50                  55

GAA AAT GAG CTA ACG TAC TAC TGC TGC AAG AAG GAC CTG TGT        344
Glu Asn Glu Leu Thr Tyr Tyr Cys Cys Lys Lys Asp Leu Cys
                60                  65

AAC TTT AAC GAA CAG CTT GAA AAT GGT GGG ACA TCC TTA TCA        386
Asn Phe Asn Glu Gln Leu Glu Asn Gly Gly Thr Ser Leu Ser
70                  75                  80

GAG AAA ACA GTT CTT CTG CTG GTG ACT CCA TTT CTG GCA GCA        428
Glu Lys Thr Val Leu Leu Leu Val Thr Pro Phe Leu Ala Ala
    85                  90                  95

GCC TGG AGC CTT CAT CCC TAA G TCAACACCAG GAGAGCTTCT            470
Ala Trp Ser Leu His Pro
        100

CCCAAACTCC CCGTTCCTGC GTAGTCCGCT TTCTCTTGCT GCCACATTCT         520

AAAGGCTTGA TATTTTCCAA ATGGATCCTG TTGGGAAAGA ATAAAATTAG         570

CTTGAGCAAC CTGGCTAAGA TAGAGGGGTC TGGGAGACTT TGAAGACCAG         620

TCCTGCCCGC AGGGAAGCCC CACTTGAAGG AAGAAGTCTA AGAGTGAAGT         670

AGGTGTGACT TGAACTAGAT TGCATGCTTC CTCCTTTGCT CTTGGGAAGA         720

CCAGCTTTGC AGTGACAGCT TGAGTGGGTT CTCTGCAGCC CTCAGATTAT         770

TTTTCCTCTG GCTCCTTGGA TGTAGTCAGT TAGCATCATT AGTACATCTT         820

TGGAGGGTGG GGCAGGAGTA TATGAGCATC CTCTCTCACA TGGAACGCTT         870

TCATAAACTT CAGGGATCCC GTGTTGCCAT GGAGGCATGC CAAATGTTCC         920

ATATGTGGGT GTCAGTCAGG GACAACAAGA TCCTTAATGC AGAGCTAGAG         970
```

-continued

```
GACTTCTGGC AGGGAAGTGG GGAAGTGTTC CAGATTCCAG ATAGCAGGGC        1020

ATGAAAACTT AGAGAGGTAC AAGTGGCTGA AAATCGAGTT TTTCCTCTGT        1070

CTTTAAATTT TATATGGGCT TTGTTATCTT CCACTGGAAA AGTGTAATAG        1120

CATACATCAA TGGTGTGTT                                          1139
```

( 2 ) INFORMATION FOR SEQ ID NO:12:

( i ) SEQUENCE CHARACTERISTICS:
( A ) LENGTH: 1980 base pairs
( B ) TYPE: Nucleic Acid
( C ) STRANDEDNESS: Double stranded
( D ) TOPOLOGY: Linear ( i i ) MOLECULE TYPE: Genomic DNA
cDNA to mRNA
( A ) DESCRIPTION: Herpesvirus saimiri mCCPH gene ( i i i ) HYPOTHETICAL: No ( i v ) ANTI-SENSE: No ( v i ) ORIGINAL SOURCE:
( A ) ORGANISM: Herpesvirus saimiri
( B ) STRAIN: #11

( v i i i ) POSITION IN GENOME:
( A ) CHROMOSOME/SEGMENT: L-DNA
( B ) MAP POSITION: 10546-12525
( C ) UNITS: Nucleotide number ( x ) PUBLICATION INFORMATION:
( A ) AUTHORS: Albrecht, Jens- Christian
Fleckenstein, Bernhard
( B ) TITLE: New Member of the Multigene Family of
Complement Control Proteins in Herpesvirus Saimiri
( C ) JOURNAL: Journal of Virology
( D ) VOLUME: 66
( E ) ISSUE: 6
( F ) PAGES: 3937-3940
( G ) DATE: June 1992

( x i ) SEQUENCE DESCRIPTION: SEQ ID NO:12:

```
AAGCTTTGTC TTTTAATTCT GTAAGTTTAC TTAGGTAATT TAATAACAAA          50

TAAACTTATA AACATATTTT AAGCTTTACT GGTATTGTTG TTTATAACCT         100

TTTTGTTTTA TACATAAAAG TTTAAGTAAG ATACTTATTT TCTAGTAGCT         150

AGTACGTTGC TTGCTCATTT TTCTAATAGT GTTTATTCTA AAACTTATAT         200

AATTTAAATA TAATTTGCAG TAACAGTTTA AAATGTTAAA CTTTTGTTAT         250

TTTTAATATG ATATATGTTA ACAGCTATAG TTGCATTTTA TATTTGTGTT         300

TTTATTAATT TAAGAAGGAT TAGTAAAATA TATTTAACTT TCTGAGAAGA         350

AATTATACAG TTAGCC ATG TAC ACT TTA CAC TAC                      384
                  Met Tyr Thr Leu His Tyr
                  -20                 -15

ATT TGT CTT GTT TTG TCA TGT GTA ATT TAT TTT GTA TGG ACT TTA AGC  432
Ile Cys Leu Val Leu Ser Cys Val Ile Tyr Phe Val Trp Thr Leu Ser
                -10                 -5                  +1

TGT CCT ACA CGT AAC CAG TAT GTT TCT GTC AAA TAT GTG AAT CTA ACT  480
Cys Pro Thr Arg Asn Gln Tyr Val Ser Val Lys Tyr Val Asn Leu Thr
         5                  10                  15

AAC TAT TCA GGC CCG TAT CCA AAC GGG ACA ACG CTA CAC GTG ACA TGC  528
Asn Tyr Ser Gly Pro Tyr Pro Asn Gly Thr Thr Leu His Val Thr Cys
     20                 25                  30

CGT GAA GGA TAT GCA AAA AGA CCA GTA CAA ACT GTT ACA TGC GTC AAT  576
Arg Glu Gly Tyr Ala Lys Arg Pro Val Gln Thr Val Thr Cys Val Asn
 35                 40                  45                  50
```

-continued

```
GGT AAC TGG ACT GTA CCT AAA AAG TGT CAG AAA AAG AAA TGT TCT ACA      624
Gly Asn Trp Thr Val Pro Lys Lys Cys Gln Lys Lys Lys Cys Ser Thr
                 55                  60                  65

CCG CAA GAT CTT TTA AAT GGA AGA TAT ACT GTA ACT GGT AAT TTA TAT      672
Pro Gln Asp Leu Leu Asn Gly Arg Tyr Thr Val Thr Gly Asn Leu Tyr
             70                  75                  80

TAC GGT TCA GTT ATC ACT TAT ACT TGT AAT TCA GGC TAC AGC TTA ATT      720
Tyr Gly Ser Val Ile Thr Tyr Thr Cys Asn Ser Gly Tyr Ser Leu Ile
         85                  90                  95

GGA AGC ACA ACA TCA GCT TGT TTA CTT AAA CGA GGT GGT CGT GTT GAC      768
Gly Ser Thr Thr Ser Ala Cys Leu Leu Lys Arg Gly Gly Arg Val Asp
    100                 105                 110

TGG ACT CCA CGA CCT CCA ATT TGT GAC ATT AAA AAA TGT AAA CCT CCT      816
Trp Thr Pro Arg Pro Pro Ile Cys Asp Ile Lys Lys Cys Lys Pro Pro
115                 120                 125                 130

CCA CAA ATA GCT AAT GGG ACT CAC ACT AAT GTC AAA GAT TTC TAT ACT      864
Pro Gln Ile Ala Asn Gly Thr His Thr Asn Val Lys Asp Phe Tyr Thr
                135                 140                 145

TAT TTA GAT ACA GTT ACG TAC TCA TGC AAT GAC GAA ACA AAG TTA ACT      912
Tyr Leu Asp Thr Val Thr Tyr Ser Cys Asn Asp Glu Thr Lys Leu Thr
            150                 155                 160

TTA ACA GGC CCT TCA TCG AAA CTT TGT TCA GAA ACT GGC TCA TGG GTA      960
Leu Thr Gly Pro Ser Ser Lys Leu Cys Ser Glu Thr Gly Ser Trp Val
        165                 170                 175

CCT AAT GGA GAA ACT AAG TGT GAA TTT ATA TTT TGT AAA CTA CCT CAA     1008
Pro Asn Gly Glu Thr Lys Cys Glu Phe Ile Phe Cys Lys Leu Pro Gln
    180                 185                 190

GTT GCG AAT GCG TAC GTT GAA GTT AGA AAG TCA GCT ACG AGC ATG CAA     1056
Val Ala Asn Ala Tyr Val Glu Val Arg Lys Ser Ala Thr Ser Met Gln
195                 200                 205                 210

TAT TTG CAT ATA AAT GTT AAA TGT TAT AAA GGA TTT ATG CTA TAT GGA     1104
Tyr Leu His Ile Asn Val Lys Cys Tyr Lys Gly Phe Met Leu Tyr Gly
                215                 220                 225

GAA ACT CCT AAT ACG TGT AAC CAT GGA GTA TGG TCT CCA GCT ATT CCT     1152
Glu Thr Pro Asn Thr Cys Asn His Gly Val Trp Ser Pro Ala Ile Pro
            230                 235                 240

GAA TGT ATG AAG ATA TCT TCT CCA AAA GGA GAC ATG CCT GGC ATA AAC     1200
Glu Cys Met Lys Ile Ser Ser Pro Lys Gly Asp Met Pro Gly Ile Asn
        245                 250                 255

TCA AAT GAA GAT AAT TCT ACA CCT TCA GGT AGG ATA TGC AAT GGA AAT     1248
Ser Asn Glu Asp Asn Ser Thr Pro Ser Gly Arg Ile Cys Asn Gly Asn
    260                 265                 270

TGT ACA ACT AGC ATG CCC ACT CAA ACA TAT ACA ATA ATT ACT GCG CGC     1296
Cys Thr Thr Ser Met Pro Thr Gln Thr Tyr Thr Ile Ile Thr Ala Arg
275                 280                 285                 290

TAT ACA AGT CAC ATA TAT TTC CCT ACT GGG AAA ACC TAT AAA CTT CCT     1344
Tyr Thr Ser His Ile Tyr Phe Pro Thr Gly Lys Thr Tyr Lys Leu Pro
                295                 300                 305

CGG GGA GTT CTA GTA ATT ATT CTT ACC ACA AGC TTT ATT ATT ATT GGA     1392
Arg Gly Val Leu Val Ile Ile Leu Thr Thr Ser Phe Ile Ile Ile Gly
            310                 315                 320

ATA ATA CTT ACT GGA GTG TGT TTA CAC AGG TGC AGA GTG TGC ATG TCC     1440
Ile Ile Leu Thr Gly Val Cys Leu His Arg Cys Arg Val Cys Met Ser
        325                 330                 335

GGG CAG TAACTACCCA ATTTCTTCAT AAATATGAGA ATCTCCGTTA CAAGTTCTTA      1496
Gly Gln
    340

ACTGGCCATA ATCCACACGA GAAGCATCTA AACGAGTATA CGCTCCGCAT              1546

CCATCATCAT ACATATCATC TTCTGGATAG CAAACATCAT CATATATAGA              1596
```

-continued

```
GTCATTTAAA CTAGTTGTAT TTCTATTACA TTCTTCTGAA AGTGGTTGAA     1646

TTTCTTCATA AACTGGGTCA TTAGAATAAT TGTTTTCTTC TGCTTGTAAT     1696

AGCTTGTGTT TTGCCTTCAA GTGAAATAAA AAAATTTCAG TCATAATTTT     1746

TAAAAAAATA TAGAAGTTTC AGTAAATTGT TGTACTTACC AAACAAGCAC     1796

CCATTATTAG TCTTGGTAGC AGCTAGAATA AATCACTTTA AGTTTAAAAG     1846

TTTAAAAATT TCCTGTCAAT GTGGTTTGCT TGGAACAAGG TGTCTACTTA     1896

GGATGTGAGT CATTTACTCT TTGAAGTTCA AAAAAAATAA CATAGTTAAA     1946

AGCTAAGCCC ATTTTCAGTG ATATTTAAAA GCTT                      1980
```

( 2 ) INFORMATION FOR SEQ ID NO:13:

( i ) SEQUENCE CHARACTERISTICS:
( A ) LENGTH: 1787 base pairs
( B ) TYPE: Nucleic Acid
( C ) STRANDEDNESS: Double stranded
( D ) TOPOLOGY: Linear ( i i ) MOLECULE TYPE: Genomic DNA
cDNA to mRNA
( A ) DESCRIPTION: Herpesvirus saimiri sCCPH gene ( i i i ) HYPOTHETICAL: No ( i v ) ANTI-SENSE: No ( v i ) ORIGINAL SOURCE:
( A ) ORGANISM: Herpesvirus saimiri
( B ) STRAIN: #11

( v i i i ) POSITION IN GENOME:
( A ) CHROMOSOME/SEGMENT: L-DNA
( B ) MAP POSITION: 10546-11773, 11966-12525
( C ) UNITS: Nucleotide number ( x ) PUBLICATION INFORMATION:
( A ) AUTHORS: Albrecht, Jens- Christian
Fleckenstein, Bernhard
( B ) TITLE: New Member of the Multigene Family of
Complement Control Proteins in Herpesvirus Saimiri
( C ) JOURNAL: Journal of Virology
( D ) VOLUME: 66
( E ) ISSUE: 6
( F ) PAGES: 3937-3940
( G ) DATE: June 1992

( x i ) SEQUENCE DESCRIPTION: SEQ ID NO:13:

```
AAGCTTTGTC TTTTAATTCT GTAAGTTTAC TTAGGTAATT TAATAACAAA       50

TAAACTTATA AACATATTTT AAGCTTTACT GGTATTGTTG TTTATAACCT      100

TTTTGTTTTA TACATAAAAG TTTAAGTAAG ATACTTATTT TCTAGTAGCT      150

AGTACGTTGC TTGCTCATTT TTCTAATAGT GTTTATTCTA AAACTTATAT      200

AATTTAAATA TAATTTGCAG TAACAGTTTA AAATGTTAAA CTTTTGTTAT      250

TTTTAATATG ATATATGTTA ACAGCTATAG TTGCATTTTA TATTTGTGTT      300

TTTATTAATT TAAGAAGGAT TAGTAAAATA TATTTAACTT TCTGAGAAGA      350

AATTATACAG TTAGCC ATG TAC ACT TTA CAC TAC                  384
                  Met Tyr Thr Leu His Tyr
                  -20                 -15

ATT TGT CTT GTT TTG TCA TGT GTA ATT TAT TTT GTA TGG ACT TTA AGC   432
Ile Cys Leu Val Leu Ser Cys Val Ile Tyr Phe Val Trp Thr Leu Ser
                -10                 -5                  +1

TGT CCT ACA CGT AAC CAG TAT GTT TCT GTC AAA TAT GTG AAT CTA ACT   480
Cys Pro Thr Arg Asn Gln Tyr Val Ser Val Lys Tyr Val Asn Leu Thr
```

-continued 5 10 15

AAC TAT TCA GGC CCG TAT CCA AAC GGG ACA ACG CTA CAC GTG ACA TGC 528
Asn Tyr Ser Gly Pro Tyr Pro Asn Gly Thr Thr Leu His Val Thr Cys
20 25 30

CGT GAA GGA TAT GCA AAA AGA CCA GTA CAA ACT GTT ACA TGC GTC AAT 576
Arg Glu Gly Tyr Ala Lys Arg Pro Val Gln Thr Val Thr Cys Val Asn
35 40 45 50

GGT AAC TGG ACT GTA CCT AAA AAG TGT CAG AAA AAG AAA TGT TCT ACA 624
Gly Asn Trp Thr Val Pro Lys Lys Cys Gln Lys Lys Lys Cys Ser Thr
55 60 65

CCG CAA GAT CTT TTA AAT GGA AGA TAT ACT GTA ACT GGT AAT TTA TAT 672
Pro Gln Asp Leu Leu Asn Gly Arg Tyr Thr Val Thr Gly Asn Leu Tyr
70 75 80

TAC GGT TCA GTT ATC ACT TAT ACT TGT AAT TCA GGC TAC AGC TTA ATT 720
Tyr Gly Ser Val Ile Thr Tyr Thr Cys Asn Ser Gly Tyr Ser Leu Ile
85 90 95

GGA AGC ACA ACA TCA GCT TGT TTA CTT AAA CGA GGT GGT CGT GTT GAC 768
Gly Ser Thr Thr Ser Ala Cys Leu Leu Lys Arg Gly Gly Arg Val Asp
100 105 110

TGG ACT CCA CGA CCT CCA ATT TGT GAC ATT AAA AAA TGT AAA CCT CCT 816
Trp Thr Pro Arg Pro Pro Ile Cys Asp Ile Lys Lys Cys Lys Pro Pro
115 120 125 130

CCA CAA ATA GCT AAT GGG ACT CAC ACT AAT GTC AAA GAT TTC TAT ACT 864
Pro Gln Ile Ala Asn Gly Thr His Thr Asn Val Lys Asp Phe Tyr Thr
135 140 145

TAT TTA GAT ACA GTT ACG TAC TCA TGC AAT GAC GAA ACA AAG TTA ACT 912
Tyr Leu Asp Thr Val Thr Tyr Ser Cys Asn Asp Glu Thr Lys Leu Thr
150 155 160

TTA ACA GGC CCT TCA TCG AAA CTT TGT TCA GAA ACT GGC TCA TGG GTA 960
Leu Thr Gly Pro Ser Ser Lys Leu Cys Ser Glu Thr Gly Ser Trp Val
165 170 175

CCT AAT GGA GAA ACT AAG TGT GAA TTT ATA TTT TGT AAA CTA CCT CAA 1008
Pro Asn Gly Glu Thr Lys Cys Glu Phe Ile Phe Cys Lys Leu Pro Gln
180 185 190

GTT GCG AAT GCG TAC GTT GAA GTT AGA AAG TCA GCT ACG AGC ATG CAA 1056
Val Ala Asn Ala Tyr Val Glu Val Arg Lys Ser Ala Thr Ser Met Gln
195 200 205 210

TAT TTG CAT ATA AAT GTT AAA TGT TAT AAA GGA TTT ATG CTA TAT GGA 1104
Tyr Leu His Ile Asn Val Lys Cys Tyr Lys Gly Phe Met Leu Tyr Gly
215 220 225

GAA ACT CCT AAT ACG TGT AAC CAT GGA GTA TGG TCT CCA GCT ATT CCT 1152
Glu Thr Pro Asn Thr Cys Asn His Gly Val Trp Ser Pro Ala Ile Pro
230 235 240

GAA TGT ATG AAG ATA TCT TCT CCA AAA GGA GAC ATG CCT GGC ATA AAC 1200
Glu Cys Met Lys Ile Ser Ser Pro Lys Gly Asp Met Pro Gly Ile Asn
245 250 255

TCA AAT GAA GAT AAT TCT ACA CCT TCA GGT GCA GAG TGT GCA TGT CCG 1248
Ser Asn Glu Asp Asn Ser Thr Pro Ser Gly Ala Glu Cys Ala Cys Pro
260 265 270

GGC AGT AAC TAC CCA ATT TCT TCA TAAATATGAG AATCTCCGTT ACAAGTTCTT 1302
Gly Ser Asn Tyr Pro Ile Ser Ser
275 280

AACTGGCCAT AATCCACACG AGAAGCATCT AAACGAGTAT ACGCTCCGCA 1352

TCCATCATCA TACATATCAT CTTCTGGATA GCAAACATCA TCATATATAG 1402

AGTCATTTAA ACTAGTTGTA TTTCTATTAC ATTCTTCTGA AAGTGGTTGA 1452

ATTTCTTCAT AAACTGGGTC ATTAGAATAA TTGTTTTCTT CTGCTTGTAA 1502

TAGCTTGTGT TTTGCCTTCA AGTGAAATAA AAAAATTTCA GTCATAATTT 1552

-continued

| | | | | | |
|---|---|---|---|---|---|
| TTAAAAAAAT | ATAGAAGTTT | CAGTAAATTG | TTGTACTTAC | CAAACAAGCA | 1602 |
| CCCATTATTA | GTCTTGGTAG | CAGCTAGAAT | AAATCACTTT | AAGTTTAAAA | 1652 |
| GTTTAAAAAT | TTCCTGTCAA | TGTGGTTTGC | TTGGAACAAG | GTGTCTACTT | 1702 |
| AGGATGTGAG | TCATTTACTC | TTTGAAGTTC | AAAAAAAATA | ACATAGTTAA | 1752 |
| AAGCTAAGCC | CATTTTCAGT | GATATTTAAA | AGCTT | | 1787 |